(12) United States Patent
Taniguchi et al.

(10) Patent No.: US 7,928,088 B2
(45) Date of Patent: Apr. 19, 2011

(54) TH1 CELL DIFFERENTIATION ACCELERATOR

(75) Inventors: Masaru Taniguchi, Yokohama (JP); Toshinori Nakayama, Chiba (JP); Ikuya Yano, Kiyose (JP); Takashi Naka, Kiyose (JP)

(73) Assignees: Riken, Wako-shi (JP); Japan BCG Laboratory, Tokyo (JP)

( * ) Notice: Subject to any disclaimer, the term of this patent is extended or adjusted under 35 U.S.C. 154(b) by 595 days.

(21) Appl. No.: 11/939,920

(22) Filed: Nov. 14, 2007

(65) Prior Publication Data

US 2008/0182818 A1 Jul. 31, 2008

(30) Foreign Application Priority Data

Dec. 8, 2006 (JP) ................................. 2006-332387

(51) Int. Cl.
*A61K 31/70* (2006.01)

(52) U.S. Cl. ........................................................ 514/54

(58) Field of Classification Search ........................ None
See application file for complete search history.

(56) References Cited

U.S. PATENT DOCUMENTS 5,853,737 A * 12/1998 Modlin et al. ............. 424/248.1

OTHER PUBLICATIONS

Sayers et al, "Suppression of allergic airway disease using mycobacterial lipoglycans", J. Allergy Clin. Immunol. 2004; 114:302-9.*
Cella et al., *Current Opinion in Immunology*, 9: 10-16 (1997).
Dao et al., *Infection and Immunity*, 72(4): 2067-2074 (Apr. 2004).
Hunter et al., *Journal of Biological Chemistry*, 265(16): 9272-9279 (Jun. 5, 1990).
Johansson et al., *Immunology Letters*, 77: 63-66 (2001).
Moreno et al., *Clin. Exp. Immunol*, 74: 206-210 (1988).
Nigou et al., *Journal of Immunology*, 166: 7477-7485 (2001).
Reis e Sousa et al., *Journal of Experimental Medicine*, 186(11): 1819-1829 (Dec. 1, 1997).
Reis e Sousa et al., *Current Opinion in Immunology*, 11: 392-399 (1999).
Schlesinger et al., *Journal of Immunology*, 152: 4070-4079 (1994).
Sibley et al., *Infection and Immunity*, 56(5): 1232-1236 (May 1998).
Yoshida et al., *Infection and Immunity*, 65(5): 1953-1955 (May 1997).

* cited by examiner

*Primary Examiner* — Elli Peselev
(74) *Attorney, Agent, or Firm* — Leydig, Voit & Mayer, Ltd.

(57) ABSTRACT

The present invention provides an agent for promoting human Th1 cell differentiation and an agent for suppressing human Th2 cell differentiation, comprising lipoarabinomannans and/or lipomannans derived from BCG cell bodies. The agent of the present invention is useful as a prophylactic/therapeutic agent for cancers and the like, and also as a therapeutic agent for allergic diseases such as pollinosis.

14 Claims, 13 Drawing Sheets

M, Molecular Weight Marker
1, AOYAMA-B strain LAM
2, BCG-LAM/LM
3, BCG-LAM
4, BCG-LM FIG. 6
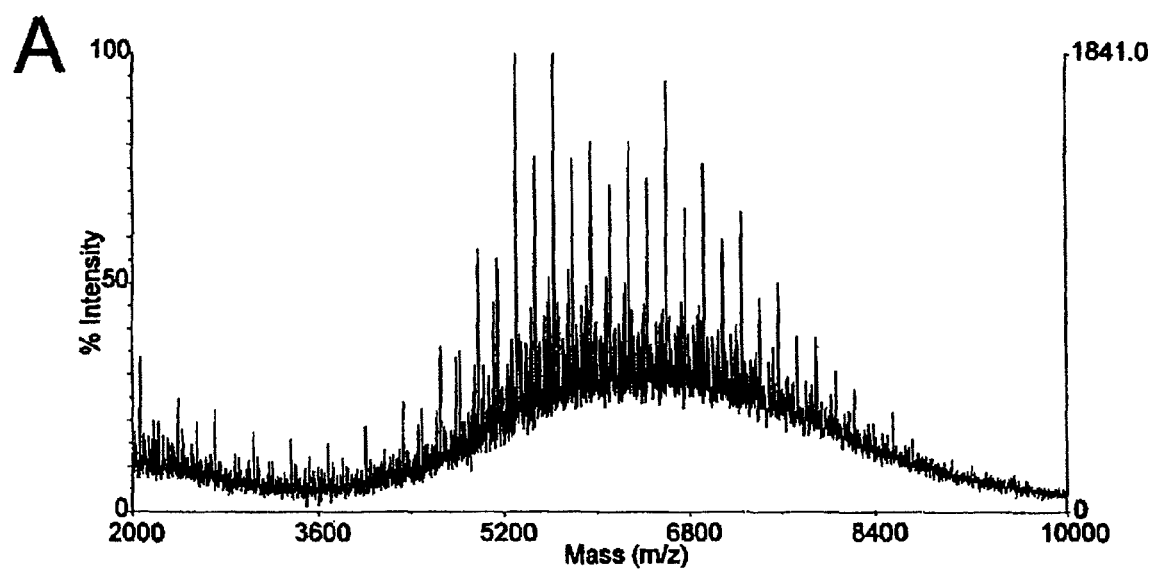
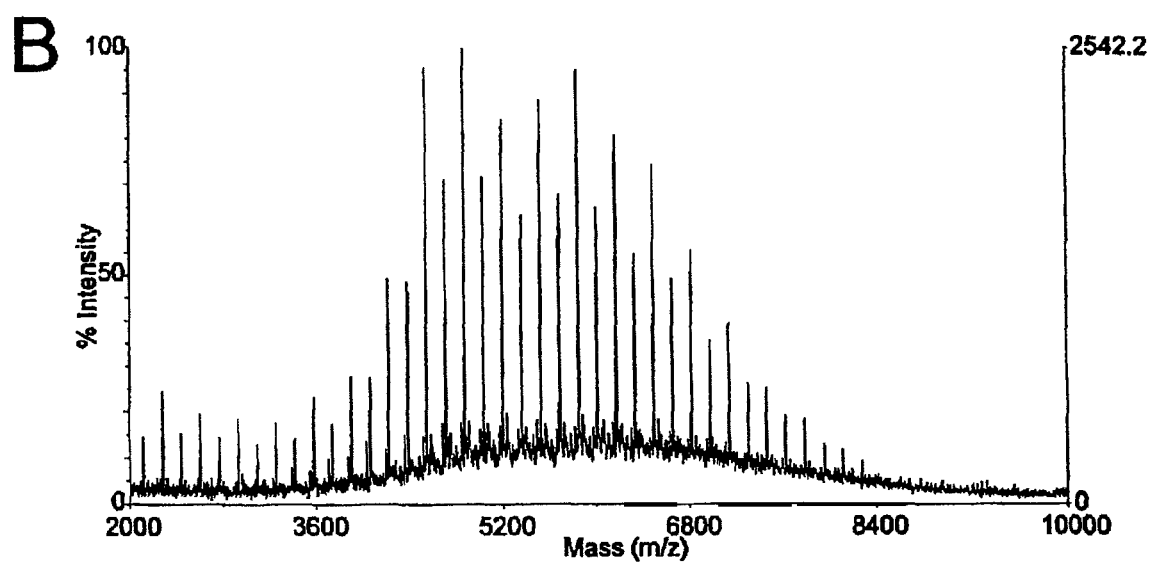

FIG. 8
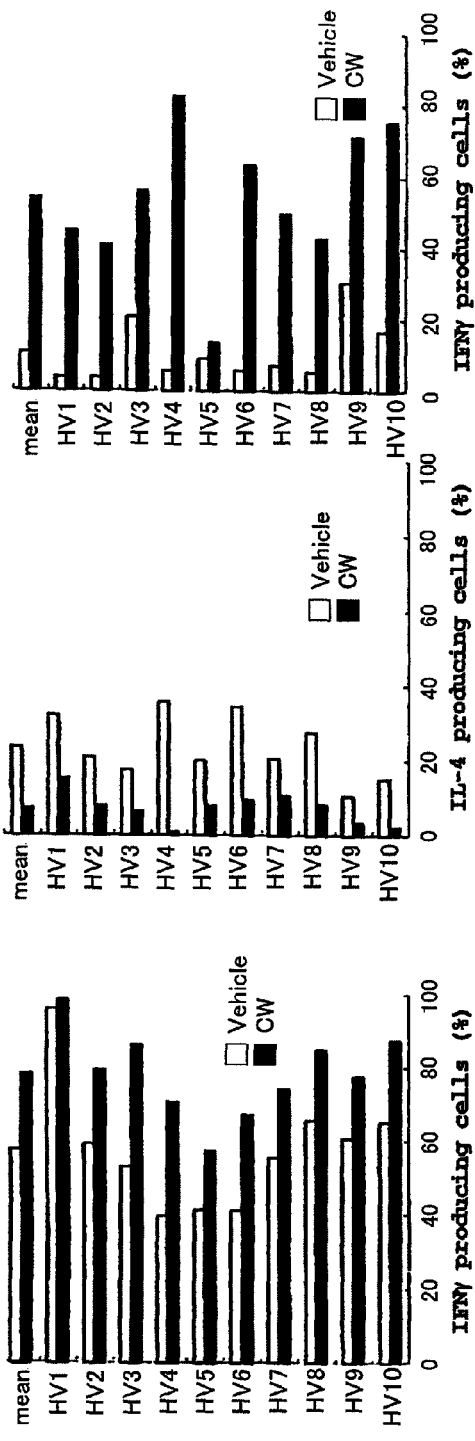
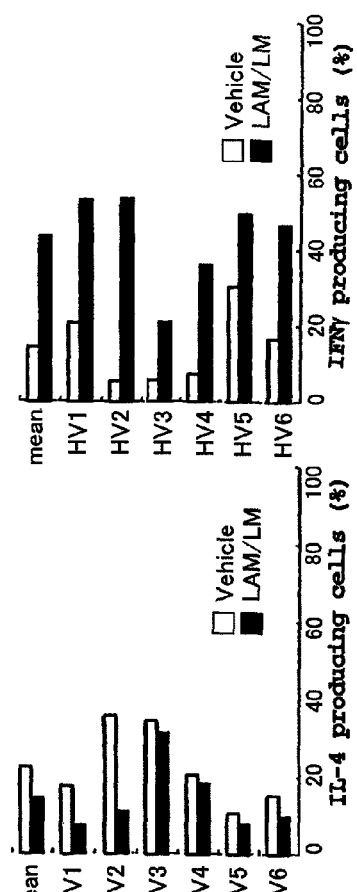
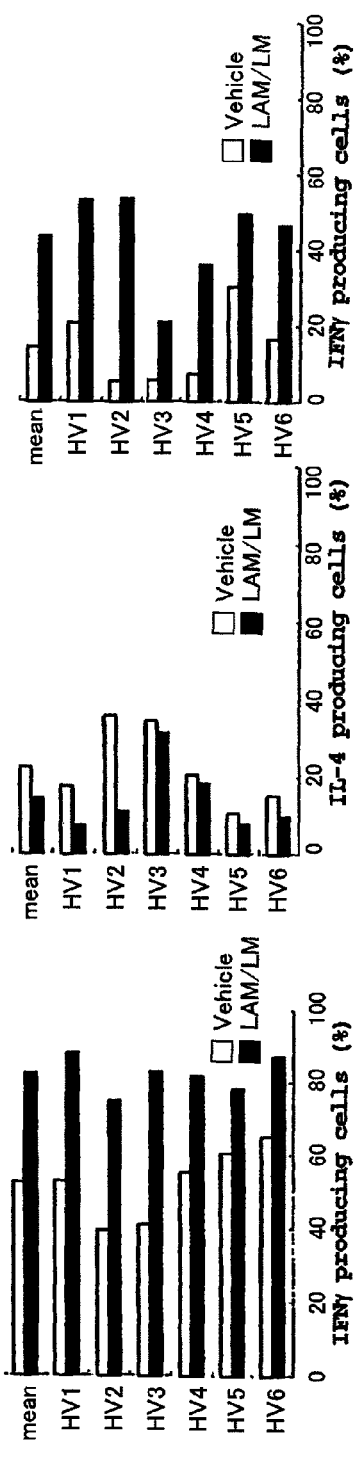

TH1 CELL DIFFERENTIATION ACCELERATOR

CROSS REFERENCE TO RELATED APPLICATION

This application is based on Japanese Patent Application 2006-332387 filed in Japan (filing date: Dec. 8, 2006), all teachings disclosed wherein are incorporated herein by reference.

TECHNICAL FIELD

The present invention relates to a use of lipoarabinomannan (LAM) and/or lipomannan (LM) derived from *Mycobacterium bovis* bacillus Calmette-Guerin (BCG) for promoting the differentiation from Th0 (naive T) cells to Th1 cells, or for suppressing the differentiation from Th0 (naive T) cells to Th2 cells.

BACKGROUND ART

The incidences of various allergic diseases, including asthma, pollinosis, food allergies, and allergic dermatitis, have recently been increasing; amid this situation, along with air pollution, stress and the like, there is a strong demand for the elucidation of the causes of these diseases and fundamental treatments. *Mycobacterium bovis* bacillus Calmette-Guerin (BCG) is an attenuated live vaccine that has been widely used as a tuberculosis vaccine all over the world for 80 years or more, and is known to suppress the onset of tuberculosis. From this fact, it is publicly known that the BCG live vaccine potently activates anti-tuberculosis immunity, that is, Th1 (cellular) immunoreactions. However, it remains unclear which component of BCG cell bodies and how it stimulates Th1 immunity to exhibit its prophylactic effect. For human applications, it is better to use an isolated cell body component with greater emphasis on safety. Although an extremely large number of therapeutic agents for allergic diseases, including steroid preparations, are available, many of them are symptomatic agents, with almost no pharmaceuticals known to be capable of preventing/treating allergic diseases by enhancing Th1 immunoreactions or suppressing Th2 immunoreactions.

Lipoarabinomannan (LAM) is a major component of the cell wall, and is thought to be a modulin that mediates a broad range of forms of immune control that are favorable for the survival of mycobacteria in infected hosts and anti-inflammatory effects. These effects include the suppression of T lymphocyte growth via antigen processing interruption (non-patent reference 1), inhibition of macrophage activation by interferon γ (non-patent reference 2), scavenging of oxygen-derived free radicals, and the like can be mentioned. LAM is not only a pathogenic factor that is responsible for macrophage inactivation, but also is involved in phagocytosis of mycobacteria in phagocytes (non-patent reference 3). Additionally, it has recently been proposed that phosphatidyl inositol mannosides (PIMs), which are thought to be precursors for lipomannan (LM) and LAM, recruit NKT cells and play a role in the initial stage of granulomatous reactions (non-patent references 4 and 5). The biosynthetic relationships among phosphatidyl inositol (PI), PIMs, LM and LAM have recently been evidenced by biochemical (non-patent references 6 and 7) and genetic (non-patent references 8 and 9) studies; however, details of this pathway remain highly deductive. However, the structures of LAM from many species, including *Mycobacterium tuberculosis, Mycobacterium leprae, Mycobacterium bovis* BCG, and *Mycobacterium smegmatis*, have been widely described in the past 10 years. LAM is a complex glycolipid composed of D-mannan and D-arabinan attached to the PI portion that anchors to the glycolipid in the mycobacterial cell wall (non-patent reference 10).

In LAM molecules, three kinds of capping motifs are known. The first is ManLAM, which has a mannosyl cap, isolated from *M. tuberculosis, Mycobacterium kansasii* and the like; the second is PILAM, which has a phosphatidyl inositol cap, isolated from *M. smegmatis* and the like; the third is AraLAM, which has no capping motif, isolated and purified from *M. chelonae* and the like.

ManLAM contributes to the persistence of mycobacteria that accumulate and grow slowly in the human body. The anti-inflammatory activity of ManLAM has been shown to require an interaction of ManLAM with mannose receptor and/or dendritic cell-specific ICAM-3 (intracellular adhesion molecule-3) grabbing non-integrin via mannose cap motifs (non-patent references 11, 12, and 13). Conversely, PILAM is capable of inducing the release of a wide variety of pro-inflammatory cytokines via activation of Toll-like receptors 2 (TLR-2) (non-patent references 14, 15, and 16). Because AraLAM exhibits no activity, this activity seems to require PI caps (non-patent reference 17). LM has been shown to activate macrophages in a TLR-2-dependent and TLR-4- and TLR-6-independent manner (non-patent references 18, 19, and 20). Therefore, the ManLAM/LM balance may be a parameter that influences the net immunoreactions against mycobacteria.

IL-12 is known to be capable of enhancing anti-tumor immunity, and suppressing Th2-related diseases such as allergic diseases, by promoting the differentiation of naive CD4T cells into Th1 cells (IFNγ-producing cells), and inhibiting the differentiation into Th2 (IL-4-producing cells) Some findings have been reported regarding these effects of LAM and LM on IL-12 production.

It is stated in non-patent reference 21 that BCG infections and the addition of Mannose-capped lipoarabinomannan (ManLAM) in the process of the differentiation from human monocytes to dendritic cells reduce subsequent IL-12 synthesis in dendritic cells, and that IL-12 p35 and p40 mRNA synthesis was more potently suppressed by ManLAM than by AraLAM.

It is stated in non-patent reference 11 that the ManLAMs derived from *Mycobacterium bovis* BCG and *Mycobacterium tuberculosis* dose-dependently suppressed LPS-induced IL-12 production by human dendritic cells, and that this inhibitory activity was lost by deleting the Mannose cap or GPI acyl residues.

It is stated in non-patent reference 22 that the AraLAM derived from a *Mycobacterium* sp. is capable of inducing IL-12 expression in mouse macrophages (J774 cell lines, intraperitoneal macrophages), whereas the ManLAM derived from the Erdman strain is incapable of inducing IL-12 expression.

It is stated in non-patent document 20 that irrespective of the kind of *Mycobacterium*, ManLAM did not induce the expression of the IL-12 gene in mouse macrophages (RAW264.7, marrow-derived macrophages), whereas PILAM induced IL-12 secretion, that non-capped LAM purified from *Mycobacterium chelonae* did not induce IL-12 secretion, and that LM potently induced IL-12 irrespective of the kind of *Mycobacterium*.

According to these findings, LAM induces IL-12 production by mouse macrophages but suppressively acts on IL-12 production by human macrophages.

The dendritic cells (DC) patrol peripheral tissues as sentinels for the immune system, and are critically important to the induction of cellular immunity against intracellular pathogens, including mycobacteria (non-patent reference 23). Much evidence has demonstrated that DCs are the major APC for the initiation of primary T cell responses as well as the initial source of IL-12 in mycobacterial infections (non-patent references 24, 25, and 26). Infections of *Mycobacterium tuberculosis* and *M. bovis* bacillus Calmette-Guerin (BCG) to human or mouse myeloid DC induce a well balanced process of cell maturation and up-regulation of IL-12 production (non-patent references 27 and 28). When BCG-infected DCs are transferred to mice, rapid IFNγ responses against the mycobacterial antigens occur (non-patent reference 27), and DCs infected with *M. tuberculosis* induce potent immunity against experimental tuberculosis in mice (non-patent reference 29).

[Non-patent reference 1] Clin. Exp. Immunol., 74, 206-210 (1988)

[Non-patent reference 2] Infect. Immun., 56, 1232-1236 (1988)

[Non-patent reference 3] J. Immunol., 152, 4070-4079 (1994)

[Non-patent reference 4] Proc. Natl. Acad. Sci. U.S.A., 96, 5141-5146 (1999)

[Non-patent reference 5] J. Biol. Chem., 276, 34896-34904 (2001)

[Non-patent reference 6] Glycobiology 5, 117-127 (1995)

[Non-patent reference 7] J. Biol. Chem., 272, 18460-18466 (1997)

[Non-patent reference 8] J. Biol. Chem., 274, 31625-31631 (1999)

[Non-patent reference 9] Biochem. J., 363, 437-447 (2002)

[Non-patent reference 10] J. Biol. Chem., 265, 9272-9279 (1990)

[Non-patent reference 11] J. Immunol., 166, 7477-7485 (2001)

[Non-patent reference 12] J. Exp. Med., 197, 7-17 (2003)

[Non-patent reference 13] Trends Microbiol., 11, 259-263 (2003)

[Non-patent reference 14] J. Biol. Chem., 272, 117-124 (1997)

[Non-patent reference 15] Infect. Immun., 61, 4173-4181 (1993)

[Non-patent reference 16] J. Immunol., 163, 6748-6755 (1999)

[Non-patent reference 17] J. Biol. Chem., 277, 30635-30648 (2002)

[Non-patent reference 18] J. Immunol., 171, 2014-2023 (2003)

[Non-patent reference 19] J. Immunol., 172, 4425-4434 (2004)

[Non-patent reference 20] Infect. Immun., 72, 2067-74 (2004)

[Non-patent reference 21] Immunol. Lett., 77, 63-6 (2001)

[Non-patent reference 22] Infect Immun., 65, 1953-5, (1997)

[Non-patent reference 23] Nature, 392, 245-252, (1998)

[Non-patent reference 24] Curr. Opin. Immunol., 9, 10-16 (1997)

[Non-patent reference 25] J. Exp. Med., 186, 1819-1829 (1997)

[Non-patent reference 26] Curr. Opin. Immunol., 11, 392-399 (1999)

[Non-patent reference 27] Eur. J. Immunol., 29, 1972-1979 (1999)

[Non-patent reference 28] Int. J. Cancer, 70, 128-134 (1997)

[Non-patent reference 29] Immunology, 99, 473-480 (2000)

DISCLOSURE OF THE INVENTION

In view of the circumstances described above, the present invention is directed to isolating and purifying a component that is active in enhancing Th1 immune responses and suppressing Th2 immune responses, contained in BCG cell bodies, to clarifying its features, and to developing it as a promoting agent for an IFNγ-producing helper T cell differentiation or a suppressing agent for an IL-4-producing helper T cell differentiation.

The present inventors diligently investigated to accomplish the above-described objects, found that the LAMs and LMs contained in BCG cell bodies are the substances responsible for the activity to enhance Th1 immune responses and suppress Th2 immune responses, and developed the present invention described below.

Accordingly, the present invention relates to the following:

[1] An agent for promoting human Th1 cell differentiation comprising lipoarabinomannans and/or lipomannans derived from BCG cell bodies.

[2] The agent described in [1] above, comprising a combination of lipoarabinomannans derived from BCG cell bodies and lipomannans derived from BCG cell bodies.

[3] The agent described in [1] above, wherein at least one of the lipomannans is a triacyllipomannan comprising 20 to 48 mannose residues.

[4] The agent described in [3] above, wherein the triacyllipomannan is a compound represented by the formula:

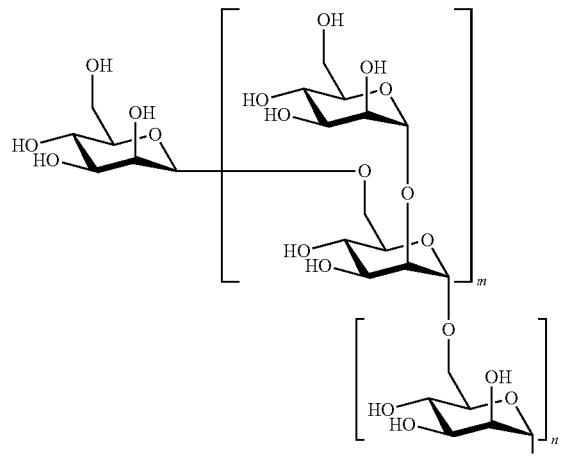

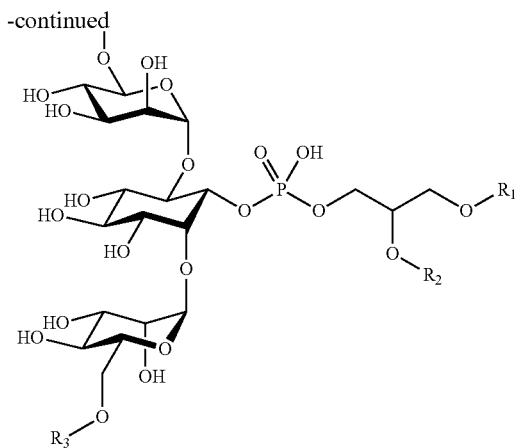

(wherein each of $R_1$, $R_2$ and $R_3$, whether identical or different, is an acyl group having 14 to 20 carbon atoms, m represents an integer of 1 to 22, and n represents an integer of 1 to 10).

[5] An agent for suppressing human Th2 cell differentiation comprising lipoarabinomannans and/or lipomannans derived from BCG cell bodies.

[6] The agent described in [5] above, comprising a combination of lipoarabinomannans derived from BCG cell bodies and lipomannans derived from BCG cell bodies.

[7] The agent described in [5] above, wherein at least one of the lipomannans is a triacyllipomannan comprising 20 to 48 mannose residues.

[8] The agent described in [7] above, wherein the triacyllipomannan is a compound represented by the formula:

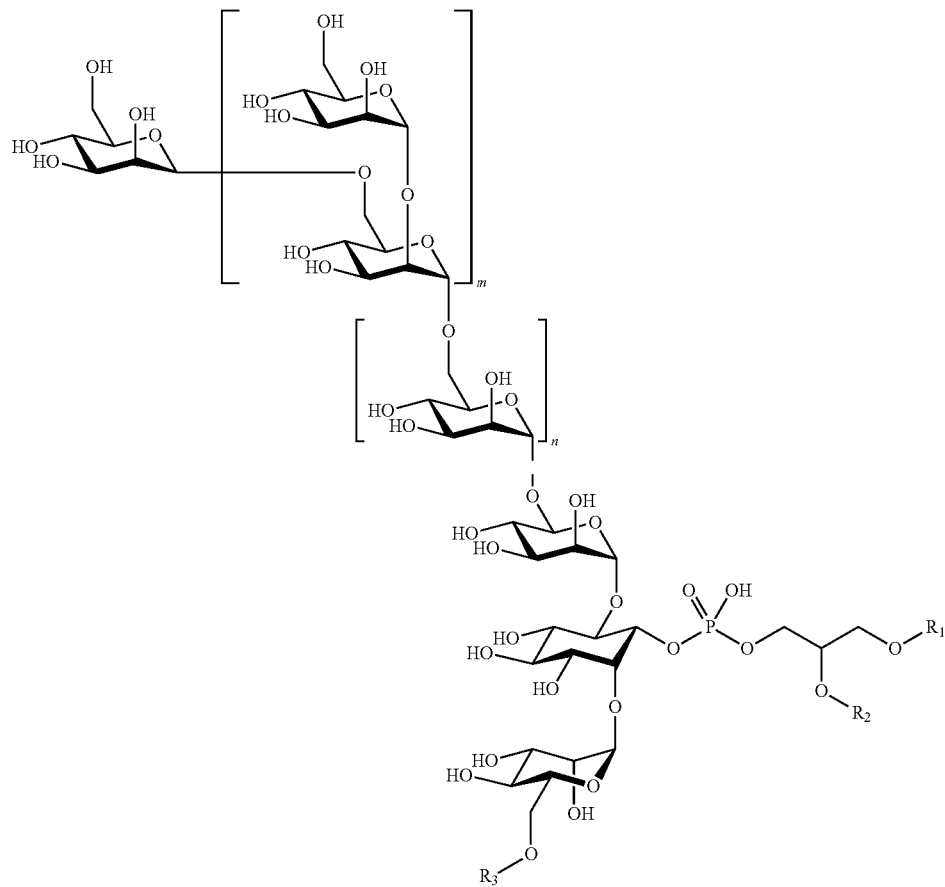

(wherein each of $R_1$, $R_2$ and $R_3$, whether identical or different, is an acyl group having 14 to 20 carbon atoms, m represents an integer of 1 to 22, and n represents an integer of 1 to 10).

[9] A method of promoting the differentiation of human CD4T cells into Th1 cells, comprising using a medium containing lipoarabinomannans and/or lipomannans derived from BCG cell bodies in antigen stimulation culture of the CD4T cells.

[10] A method of suppressing the differentiation of human CD4T cells into Th2 cells, comprising using a medium containing lipoarabinomannans and/or lipomannans derived from BCG cell bodies in antigen stimulation culture of the CD4T cells.

[11] The method described in [10] above, wherein the medium further comprises antigen-presenting cells.

[12] A method of promoting the differentiation of Th1 cells in a mammal, comprising administering an effective amount of lipoarabinomannans and/or lipomannans derived from BCG cell bodies to the mammal.

[13] A method of suppressing Th2 cell differentiation in a human, comprising administering an effective amount of lipoarabinomannans and/or lipomannans derived from BCG cell bodies to the human.

[14] A prophylactic/therapeutic agent for allergic disease, comprising lipoarabinomannans and/or lipomannans derived from BCG cell bodies.

[15] A method for preventing/treating allergic disease in a mammal, comprising administering an effective amount of lipoarabinomannans and/or lipomannans derived from BCG cell bodies to the mammal.

EFFECT OF THE INVENTION

Because the LAMs and LMs contained in BCG cell bodies enhance Th1 immune responses and suppress Th2 immune responses, they are useful as prophylactic/therapeutic agents for cancers and the like, and also as therapeutic agents for allergic diseases such as pollinosis and the like, and still also as adjuvants for prophylactic vaccines for infectious diseases, including tuberculosis.

BRIEF DESCRIPTION OF THE DRAWINGS

FIG. 6 shows MALDI-TOF mass spectra of BCG-LM. (A) MALDI-TOF mass spectrum of the acylated form of BCG-LM. (B) MALDI-TOF mass spectrum of the deacylated form of BCG-LM.

FIG. 8 shows the effects of BCG-CW and LAM/LM on human Th1/Th2 cell differentiation. HV represents each healthy human volunteer. (A) and (B): BCG-CW, (C) and (D): LAM/LM. (A) and (C): Th1 differentiation inducing conditions, (B) and (D): Th2 differentiation inducing conditions.

BEST MODE FOR CARRYING OUT THE INVENTION

Figure 1:
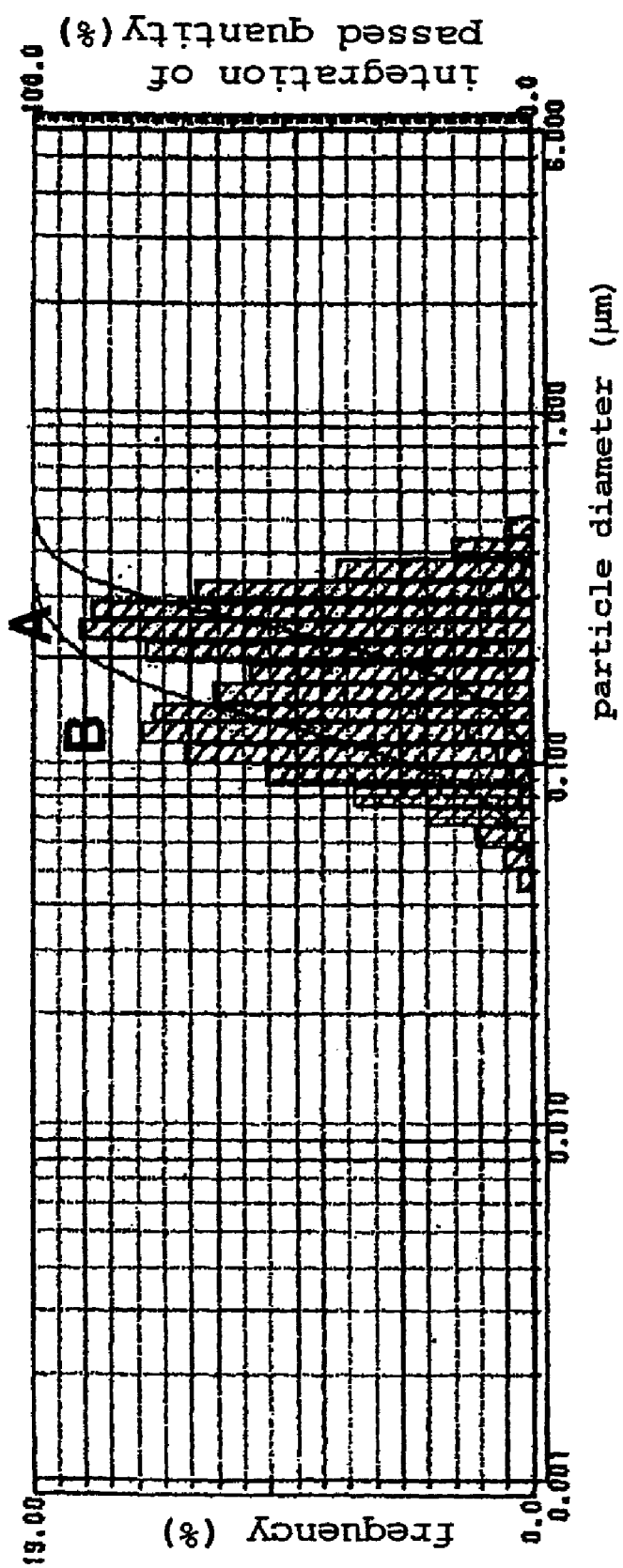
FIG. 1 shows the particle size distributions of CW (A) and CM (B).

The present invention provides an agent for promoting human Th1 cell differentiation and an agent for suppressing human Th2 cell differentiation, comprising lipoarabinomannans and/or lipomannans derived from BCG cell bodies (hereinafter referred to as the agent of the present invention).

The lipoarabinomannans (LAM) and lipomannans (LM) that can be used in the present invention are derived from BCG cell bodies. The choice of BCG strain is not particularly limited, as long as the lipoarabinomannans and/or lipomannans derived from the strain have promoting action on human Th1 cell differentiation and suppressive action on human Th2 cell differentiation, respectively; as examples of the choice, the Tokyo-172 strain, the Connaught strain, the Tice strain, the Armand-Frappier strain, the Pasteur strain, the Russian strain, the Brazilian strain, the Glaxo strain, the Prague strain, the Phipps strain and the like can be mentioned. Each BCG strain can be obtained from the American Type Culture Collection (ATCC) and elsewhere.

LAM is one of the major lipoglycans that constitute the cell walls and cell membranes of mycobacteria such as BCG. LAM usually contains a sugar backbone comprising a mannosyl phosphatidyl inositol anchor (MPI), a D-mannan core and a D-arabinan domain, and a capping motif. LAM derived from a BCG strain includes many kinds of LAMs with different numbers of sugar (for example, mannose) residues contained in the molecule thereof. An analysis of LAM derived from a BCG strain by MALDI-TOFF Mass reveals that deprotonated molecular ions $[M-H]^-$ are distributed in the range of about m/z 13000 to about m/z 17000, centering at a molecular weight of about m/z 15000.

The number of acyl groups that constitute LAM derived from a BCG strain is normally 1 to 3. Hence, the LAM includes monoacyl LAM, diacyl LAM and triacyl LAM. The acyl groups are normally acyl groups derived from a C14-20 fatty acids. As the fatty acid, myristic acid (C14:0), pentadecanoic acid (C15:0), palmitic acid (C16:0), palmitoleic acid (C16:1), heptadecanoic acid (C17:0), stearic acid (C18:0), oleic acid (C18:1), tuberculostearic acid (10-methyl C18:0) and the like can be mentioned, and the fatty acid is preferably palmitic acid (C16:0), stearic acid (C18:0) or tuberculostearic acid (10-methyl C18:0).

As the branched structure of a sugar chain contained in LAM derived from a BCG strain, terminal arabinose, 2-arabinose, 5-arabinose, 3,5-arabinose, terminal mannose, 2-mannose, 6-mannose, 2,6-mannose and the like can be mentioned, and the contents of 5-arabinose, 3,5-arabinose, terminal mannose and 2,6-mannose are relatively high. Most of the terminal structures are mannose caps, with non-cap (i.e., terminal arabinose) structures accounting for only a small percentage. The ratio of terminal mannose structures is normally not less than 10 times, preferably not less than 20 times (for example, about 40 times), that of terminal arabinose structures.

LM, like LAM, is one of the major lipoglycans that constitute the cell walls and cell membranes of mycobacteria such as BCG. LM is the precursor in the biosynthesis of LAM. LM derived from a BCG strain includes many kinds of LM with different numbers of sugar (for example, mannose) residues contained in the molecule thereof. An analysis of LMs derived from a BCG strain by MALDI-TOFF Mass reveals that deprotonated molecular ions [M-H]$^-$ are distributed in the range of about m/z 4500 to about m/z 9000, and ones containing 20 to 48 mannose residues are major components (not less than about 90% (molar ratio)).

The number of acyl groups that constitute LM derived from BCG cell bodies is normally 1 to 3. Hence, the LM includes monoacyl LM, diacyl LM and triacyl LM, and is preferably triacyl LM. The acyl group is normally an acyl group derived from a C14-20 fatty acid. As the fatty acid, myristic acid (C14:0), pentadecanoic acid (C15:0), palmitic acid (C16:0), palmitoleic acid (C16:1), heptadecanoic acid (C17:0), stearic acid (C18:0), oleic acid (C18:1), tuberculostearic acid (10-methyl C18:0) and the like can be mentioned, and the fatty acid is preferably palmitic acid (C16:0), stearic acid (C18:0) or tuberculostearic acid (10-methyl C18:0).

As the branched structure of a sugar chain contained in LM derived from a BCG strain, terminal arabinose, terminal mannose, 2-mannose, 6-mannose, 2,6-mannose, and the like can be mentioned, and the contents of terminal mannose, 6-mannose and 2,6-mannose are relatively high. Most of the terminal structures are mannose caps, with non-cap (i.e., terminal arabinose) structures accounting for only a small percentage. The ratio of terminal mannose structures is normally not less than 50 times, preferably not less than 100 times (for example, about 360 times), that of terminal arabinose structures.

Preferably at least a part of the LMs that can be used in the present invention are triacyl LM comprising 20 to 48 mannose residues. As the triacyl LM, a compound represented by:

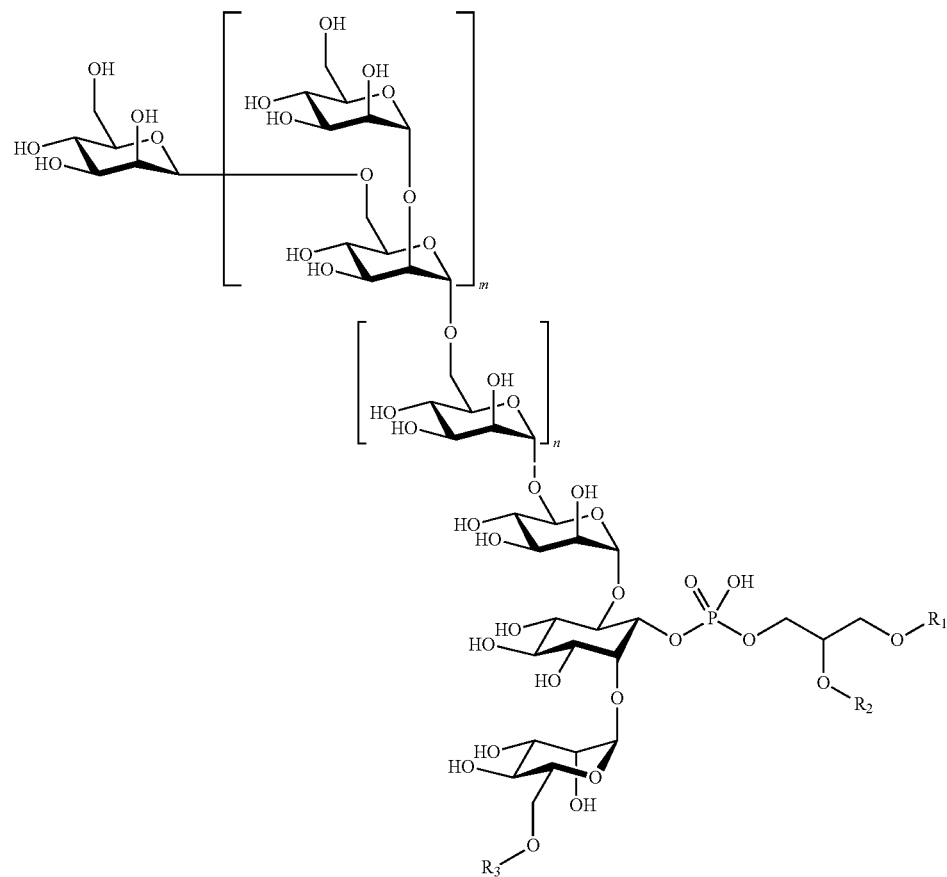

(wherein each of $R_1$, $R_2$ and $R_3$, whether identical or different, is an acyl group having 14 to 20 carbon atoms, m represents an integer of 1 to 22, and n represents an integer of 1 to 10) can be mentioned.

As the acyl groups for $R_1$ to $R_3$, the above-described ones can be mentioned. Of the compounds mentioned above, those that are found at high contents are compounds wherein two of the acyl groups for $R_1$ to $R_3$ are palmitic acid (C16:0)-derived acyl groups and the remaining one is a tuberculostearic acid (10-methyl C18:0)-derived acyl group. More preferably, $R_1$ is a tuberculostearic acid-derived acyl group, and $R_2$ and $R_3$ are palmitic acid-derived acyl groups.

LAM and LM can be isolated and purified from BCG cell bodies in accordance with the methods described in Examples below and the like. For example, BCG cell bodies are homogenated using a French press and the like, and a cell wall (CW) fraction and/or the cell membrane (CM) is separated. The CW and/or CM obtained are enzymatically treated with a decomposing enzyme such as a amylase, DNase I, RNase, or trypsin, to remove proteins, nucleic acids, and glucans. The extract after the reaction is subjected to phenol extraction. Next, the glycans are removed using a hydrophobic interaction column, whereby a fraction containing LAM and LM can be obtained. Furthermore, the fraction is applied to a gel filtration column, whereby purified LAM and LM can be obtained. For details of methods of purifying LAM and LM from BCG cell bodies, see J. Biol. Chem., 271, 28682-28690 (1996), FEMS Immunol. Med. Microbiol., 24, 11-17 (1999), J. Biol. Chem., 277, 31722-31733 (2002), J. Bacteriol., 187, 854-861 (2005) and the like.

Because LAM and LM derived from BCG cell bodies promote human Th1 cell differentiation and suppress human Th2 cell differentiation, they are useful as agents for promoting human Th1 cell differentiation and agents for suppressing human Th2 cell differentiation. By administering an effective amount of LAM and/or LM derived from BCG cell bodies to a human, Th1 cell differentiation is promoted and Th2 cell differentiation is suppressed in the human. As mentioned herein, Th1 cells refer to CD4T cells that have been differentiated from naive CD4T cells and predominantly produce IFNγ. Th2 cells refer to CD4T cells that have been differentiated from naive CD4T cells and predominantly produce IL-4. Naive CD4T cells refer to CD4T cells taken out from the thymus, and remaining intact with respect to antigen stimulation; for example, peripheral CD4-positive CD45RO-negative ($CD4^+CD45RO^-$) cells and CD4-positive CD45RA-positive ($CD4^+CD45RA^+$) cells correspond thereto. Th1 cell differentiation refers to the differentiation of Th1 cells from naive CD4T cells, and Th2 cell differentiation refers to the differentiation of Th2 cells from naive CD4T cells. Th1 cell differentiation can be induced by stimulating naive CD4T cells with an antigen in the presence of IL-2 and IL-12. Th2 cell differentiation can be induced by stimulating naive CD4T cells with an antigen in the presence of IL-2 and IL-4. Th1 cell differentiation and Th2 cell differentiation are normally induced in a certain percentage of naive CD4T cells. "Promotion of differentiation" refers to increasing this percentage, and "suppression of differentiation" refers to reducing this percentage. Hence, LAM and LM derived from BCG cell bodies are capable of increasing the percentage of cells that differentiate from naive CD4T cells to Th1 cells, and decreasing the percentage of cells that differentiate from naive CD4T cells to Th2 cells.

The agent of the present invention can comprise, in addition to an effective amount of BCG-derived LAM and/or LM, an optionally chosen carrier, for example, a pharmaceutically acceptable carrier.

As examples of the pharmaceutically acceptable carrier, excipients such as sucrose, starch, mannito, sorbit, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrants such as starch, carboxymethylcellulose, hydroxypropyl starch, sodium-glycol-starch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin ammonium salt, glycine, and orange flour; preservatives such as sodium benzoate, sodium hydrogen sulfite, methylparaben, and propylparaben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao butter, polyethylene glycol, and kerosene; and the like can be mentioned, but these are not to be construed as limiting.

The agent of the present invention is preferably prepared as a dosage form that ensures a desired effect. For example, preparations suitable for oral administration are liquids prepared by dissolving an effective amount of a substance in a diluent such as water or physiological saline, capsules, saches or tablets containing an effective amount of a substance in the form of solids or granules, suspensions prepared by suspending an effective amount of a substance in an appropriate dispersant, emulsions prepared by dispersing and emulsifying a solution of an effective amount of a substance in an appropriate dispersant, and the like.

Preparations suitable for parenteral administration (for example, subcutaneous injection, intramuscular injection, topical injection, intraperitoneal administration and the like) are aqueous and non-aqueous isotonic sterile injectable liquids, which may contain an antioxidant, a buffer solution, a bacteriostatic agent, an isotonizing agent and the like. Aqueous and non-aqueous sterile suspensions can also be mentioned, which may contain a suspending agent, a solubilizer, a thickening agent, a stabilizer, an antiseptic and the like. These preparations can be enclosed in containers such as ampoules and vials for unit dosage or a plurality of dosages. It is also possible to freeze-dry the active ingredient and a pharmaceutically acceptable carrier, and store the preparation in a state that may be dissolved or suspended in an appropriate sterile vehicle just before use.

The active ingredient content in the agent of the present invention can be set as appropriate considering the choice of active ingredient, dosage form and the like, as long as the desired pharmacological effect can be obtained, and the content is normally 0.01 to 100% by weight.

The amount of the agent of the present invention applied varies depending on the activity and choice of the active ingredient, seriousness of the disease, animal species of the subject of application, drug tolerance, body weight, and age of the subject of application, and the like, and is normally about 0.0001 to about 5000 mg/kg, based on the amount of active ingredient per day for an adult.

The agent of the present invention is useful as, for example, a medicine or investigational reagent. While producing large amounts of IFNγ and enhance anti-tumor immunity and anti-viral immunity, Th1 cells suppressively act on Th2 reactions such as allergic reactions. Th2 cells produce large amounts of IL-4 and exacerbate allergic reactions and the like. Because BCG-derived LAM and/or LM is capable of promoting Th1 cell differentiation and suppressing Th2 cell differentiation, they are useful as prophylactic/therapeutic drugs for cancers (lung cancer, gastric cancer, colic cancer, liver cancer, Hodgkin's disease and the like), viral diseases (hepatitis, influenza and the like), allergic diseases (particularly diseases mediated by type I allergic reactions, such as allergic asthma, pollinosis, atopic dermatitis, eczema, food hypersensitivity, urticaria, allergic rhinitis, and allergic conjunctivitis), autoimmune diseases (type 1 diabetes mellitus, SLE, thyroiditis, autoimmune neuritis) and the like, adjuvants for prophylactic vaccines for infectious diseases including tuberculosis, and the like.

Here, as shown in an Example below, by using BCG-derived LAM and LM in combination, their promoting action on Th1 cell differentiation and suppressive action on Th2 cell differentiation can be synergistically enhanced. Therefore, by using appropriate amounts of BCG-derived LAM and BCG-derived LM in a blend or in combination, an excellent agent for promoting Th1 cell differentiation and an agent for suppressing a Th2 cell differentiation can be prepared. Accordingly, in a preferred embodiment, the agent of the present invention includes a combination of BCG-derived LAM and BCG-derived LM.

When the above-described BCG-derived LAM and BCG-derived LM are used in combination, the timing of administration of LAM and LM is not limited; LAM and LM may be simultaneously administered to a subject of administration, and may be administered at a time lag. The doses of LAM and LM are not particularly limited, as long as prophylaxis/treatment for the above-described diseases can be achieved when used in the combination agent of the present invention, and can be chosen as appropriate according to the subject of administration, route of administration, disease, combination and the like.

The manner of administration of LAM and LM is not particularly limited, as long as LAM and LM are combined at the time of administration. As examples of such a manner of administration, (1) administration of a single preparation obtained by simultaneously preparing LAM and LM, (2) simultaneous administration of two kinds of preparations obtained by separately preparing LAM and LM via a single route of administration, (3) time staggered administration of two kinds of preparations obtained by separately preparing LAM and LM via a single route of administration, (4) simultaneous administration of two kinds of preparations obtained by separately preparing LAM and LM via different routes of administration, (5) time staggered administration of two kinds of preparations obtained by separately preparing LAM and LM via different routes of administration (for example, administration in the order of LAM→LM, or administration in the reverse order) and the like can be mentioned. Hereinafter, these modes of administration are written for short as the combination agent of the present invention together.

The combination agent of the present invention, like the above-described agent of the present invention, can be prepared by mixing with a pharmaceutically acceptable carrier, according to a conventional method.

The LAM and LM contents in the combination agent of the present invention can be set as appropriate considering the choice of active ingredient, dosage form and the like, as long as the desired pharmacological effect can be obtained, and the contents are normally 0.01 to 99.99% by weight.

Although the blending ratio of LAM and LM in the combination agent of the present invention can be determined as appropriate according to the subject of administration, route of administration, disease and the like, the ratio is preferably determined so that their promoting action on Th1 cell differentiation and/or suppressive action on Th2 cell differentiation can be synergistically enhanced. The blending ratio of LAM and LM falls in the range of normally 20:1 to 1:20, preferably 10:1 to 1:10, more preferably 5:1 to 1:5 (for example, 2:1), based on the LAM:LM ratio by weight.

The dose of the combination agent of the present invention varies depending on the route of administration, symptoms, patient age and the like, and can be chosen as appropriate. The doses of LAM and LM in the combination agent of the present invention are the same as those in the agent of the present invention; because their actions and effects are synergistically enhanced by the combination, the dose of each for obtaining actions and effects equivalent to those with the use of LAM or LM alone can be a dose lower than the dose for a monotherapy, for example, not more than 50%, preferably not more than 25%, of the dose for a monotherapy.

When LAM and LM are prepared into separate preparations, their contents may be the same as the contents in the mixture preparation.

When LAMs and LMs are prepared into separate preparations and administered in combination, a pharmaceutical composition comprising LAMs and a pharmaceutical composition comprising LMs may be simultaneously administered, but prior administration of a pharmaceutical composition comprising LMs may be followed by administration of a pharmaceutical composition comprising LAMs, and prior administration of a pharmaceutical composition comprising LAMs may be followed by administration of a pharmaceutical composition comprising LM. When LAMs and LMs are administered at a time lag, the time lag varies depending on active ingredient, dosage form, and method of administration, and is, for example, within 1 minute to 3 days, preferably within 10 minutes to 1 day, more preferably within 15 minutes to 1 hour.

The present invention also provides a method of promoting the differentiation of human CD4T cells into Th1 cells, and a method of suppressing the differentiation of the CD4T cells into Th2 cells, comprising using a medium comprising lipoarabinomannans and/or lipomannans derived from BCG cell bodies in antigen stimulation culture of the CD4T cells.

The CD4T cells used in the methods of the present invention are preferably naive CD4T cells.

As used herein, the term antigen comprehensively means substances capable of being recognized by an antigen receptor (for example, T cell receptor) on cultured cells, and stimulating the cells via the receptor. Examples of the antigen not only include antigen molecules such as peptides, proteins, lipids, and glycolipids, but also include antigen mimics such as agonistic antibodies that recognize immunologically non-self cells, antigen receptor component molecules (CD3, TCRβ, TCRα and the like) and side-stimulant molecules (CD28 and the like) (for example, anti-human CD3 antibody OKT-3 and the like), and super-antigens.

The antigen stimulation culture can comprise another factor, in addition to the antigen. As the factor, T cell growth factors such as IL-2 can be mentioned. In the method of promoting the differentiation into Th1 cells, the antigen stimulation culture is preferably performed in the presence of IL-12 in order to promote the differentiation; however, even in the presence of IL-4, it is possible to promote the differentiation into Th1 cells by the methods of the present invention. To eliminate the influence of IL-4 produced by T cells in the culture, the antigen stimulation culture preferably comprises a neutralizing antibody against IL-4. In the method of suppressing the differentiation into Th2 cells, the antigen stimulation culture can be performed in the presence of IL-4. To eliminate the influence of IFNγ produced by T cells in the culture, the antigen stimulation culture preferably comprises a neutralizing antibody against IFNγ. The concentrations of these factors (IL-2, IL-12, IL-4, anti-IL-4 antibody, anti-INFγ antibody) in the medium are well known to those skilled in the art.

As examples of the medium used in the methods of the present invention, basal media (minimal essential medium (MEM), Dulbecco's modified minimal essential medium (DMEM), RPMI1640 medium, 199 medium) that may contain appropriate additives (serum, albumin, buffering agent, amino acid and the like), and the like can be mentioned. The pH of the culture broth is normally about 6 to 8, cultivation temperature is normally about 30 to 40° C., and cultivation time is normally 1 to 10 days.

The concentration of LAM and/or LM added to the medium is not particularly limited, as long as it is a concentration capable of promoting the differentiation of CD4T cells into Th1 cells, and suppressing the differentiation of CD4T cells into Th2 cells, and the concentration is, for example, 0.1 to 1000 µg/ml, preferably 10 to 500 µg/ml.

As described above, by using BCG-derived LAM and LM in combination, it is possible to synergistically enhance the promoting action on Th1 cell differentiation and suppressive action on Th2 cell differentiation. In this case, the concentrations of LAM and LM in the medium are the same as those described above; because their actions and effects are synergistically enhanced by the combination, the concentration of each for obtaining actions and effects equivalent to those with the use of LAM or LM alone can be a concentration lower than the concentration for mono-administration, for example, not more than 50%, preferably not more than 25%, of the concentration for mono-administration. The blending ratio of LAM and LM falls in the range of normally 20:1 to 1:20, preferably 10:1 to 1:10, more preferably 5:1 to 1:5 (for example, 2:1), based on the LAM:LM ratio by weight.

As shown in an Example below, to ensure that BCG-derived LAM and LM exhibit promoting action on Th1 cell differentiation, antigen-presenting cells are not required; however, to ensure that they exhibit suppressive action on Th2 cell differentiation, antigen-presenting cells are required. Therefore, in the method of suppressing the differentiation of CD4T cells into Th2 cells, the medium preferably further comprise antigen-presenting cells. As mentioned herein, an antigen-presenting cell refers to a cell that presents an antigen to lymphocytes to promote lymphocyte activation. Usually, antigen-presenting cells are dendritic cells or macrophages, which are capable of presenting antigens to T cells and NKT cells. Particularly, dendritic cells have the potent capability of antigen presentation, and are capable of presenting antigens via MHC Class I, MHC Class I-like molecules (CD1 and the like), MHC Class II and the like, expressed on the cell surface, to activate T cells or NKT cells, and are therefore preferably used in the present invention.

The antigen-presenting cells can be those derived from an optionally chosen mammal. As the mammal, humans and non-human mammals can be mentioned. As examples of the non-human mammals, laboratory animals such as mice, rats, hamsters, guinea pigs, and other rodents, as well as rabbits, domestic animals such as pigs, bovines, goat, horses, and sheep, companion animals such as dogs and cats, and primates such as monkeys, orangutans, and chimpanzees can be mentioned.

The genotype of the antigen-presenting cells used in the methods of the present invention is not particularly limited, and is normally syngeneic, allogeneic or xenogeneic, preferably syngeneic or allogeneic, more preferably syngeneic, to the human CD4T cells to be cultured.

Antigen-presenting cells can be isolated from tissues (for example, lymph nodes, spleen, peripheral blood and the like) of the above-described mammals by a method known per se. For example, dendritic cells can be isolated using an antibody against a cell surface marker that is specifically expressed on antigen-presenting cells, by means of a cell sorter, panning, the antibody magnetic bead method and the like. When dendritic cells are isolated as antigen-presenting cells, examples of the cell surface marker that is specifically expressed on dendritic cells include CD11c, MHC Class I, MHC Class I-like molecules (CD1 and the like), MHC Class II, CD8α, CD85k, CD86, FDL-M1, DEC-205 and the like.

Antigen-presenting cells can also be produced by culturing bone marrow cells, mononucleocytes and the like of the above-described mammals under appropriate antigen-presenting cell differentiation conditions. For example, bone marrow cells differentiate into dendritic cells (bone marrow-derived dendritic cells: BMDC) when cultured in the presence of GM-CSF (and also IL-4 in some cases) for about 6 days (Nature, 408, p. 740-745, 2000). By culturing mononuclear cells (particularly monocytes, macrophages and the like) in peripheral blood in the presence of GM-CSF (and also IL-2 and/or IL-4 in some cases), dendritic cells can be obtained (Motohasi S, Kobayashi S, Ito T, Magara K K, Mikuni O, Kamada N, Iizasa T, Nakayama T, Fujisawa T, Taniguchi M., Preserved IFN-alpha production of circulating Valpha24 NKT cells in primary lung cancer patients., Int J Cancer, 2002, Nov. 10; 102(2): 159-165. Erratum in: Int J. Cancer. 2003, May 10; 104(6): 799).

Promotion of differentiation into Th1 cells and suppression of differentiation into Th2 cells can be confirmed by comparing IFNγ and IL-4 production in CD4T cells in the culture with a control (CD4T cells cultured in a medium without BCG-derived LAM and LM). IFNγ and IL-4 production can be measured by intracellular staining with anti-IFNγ antibody and anti-IL-4 antibody and flowcytometric analysis.

The methods of the present invention are useful in developing new therapeutic targets and therapeutic drugs for cancers, viral diseases, and allergic diseases by analyzing the effects of BCG-derived LAM and LM on Th1/Th2 differentiation, and identifying the molecules involved in the effects.

The disclosures in all publications mentioned herein, including patents and patent application descriptions, are incorporated by reference herein in the present invention to the extent that all of them have been given expressly.

The present invention is hereinafter described in more detail by means of the following Examples, but this invention is not limited to the examples below and the like.

EXAMPLES

Example 1

1. Materials and Methods 1.1. Bacterial Strains and Growth Conditions

The *Mycobacterium bovis* BCG Tokyo 172 strain (ATCC 35737) was used. *Mycobacterium bovis* BCG Tokyo 172 was grown at 37° C. on Sauton medium for several days.

1.2. Preparation of BCG Cell Wall Fraction and Cell Membrane Fraction

Thermally killed cell bodies of BCG Tokyo 172 were suspended in a 10-fold volume of purified water, and homogenized using a French press, after which unhomogenized cells were removed via ultracentrifugation at 6760×g, and a cell wall fraction (CW) and a supernatant cell membrane fraction (CM) were separated via further ultracentrifugation at 18000×g. The separated fractions underwent measurements of the particle diameters thereof using a particle size analyzer, and the results were compared with those for BCG cell bodies.

1.3. Isolation and Purification of BCG Cell Body Phospholipids (PIM2, PIM6)

Each lipid was isolated and purified from a total lipid fraction extracted from thermally killed cell bodies of BCG with a chloroform-methanol (2:1, v/v) mixed solvent by solvent fractionation and thin-layer chromatography. Each phospholipid was identified by molecular weight determination by MALDI-TOF Mass.

1.4. Isolation and Purification of LAM and LM

CM was treated with enzymes α-amylase, DNase I, RNase, trypsin) to remove proteins, nucleic acids and glucans, and phenol extraction was performed, after which glycans were removed using a hydrophobic interaction column (Octyl Sepharose 4 Fast Flow, Amersham Biosciences) or Triton X-114 (SIGMA) to yield a crude LAM/LM fraction. The mixing ratio of LAM and LM in this crude LAM/LM was LAM:LM=about 2:1 (ratio by weight).

LAM and LM were obtained by fractionating the crude LAM/LM fraction using a gel filtration column (Superdex 75 prep grade or Sephacryl S-200, Amersham Biosciences). Each eluted fraction was subjected to silver staining and PAS staining on SDS-PAGE gel (15 to 25%), and its mobility was compared with that of LAM derived from the tubercle bacillus *M. tuberculosis* AOYAMA-B strain (produced by nacalai tesque) as the reference standard, whereby the LAM and LM were identified. Furthermore, the mannose, arabinose and myo-innositol contents of each eluted fraction were quantified by GC/MS. By MALDI TOF-MS (Voyager DE), mass analysis was performed on LAM derived from the *M. tuberculosis* AOYAMA-B strain and LAM and LM from BCG Tokyo 172.

1.5. Preparation of Human PBMC and Crude Naive CD4T Cells

Separation of human naive CD4T cells was performed using an automated magnetic cell sorter (autoMACS Miltenyi Biotec GmbH) by the method described below. Whole blood was drawn by venous paracentesis from six healthy donor volunteers at 24 to 50 years of age. 50 ml of human peripheral blood was diluted two fold with 50 ml of a D-PBS solution (Sigma-Aldrich Inc). Next, 25 ml of the above-described diluted peripheral blood was gradually overlain in four centrifugal tubes containing 12.5 ml of Ficoll-Paque Plus (Amersham Biosciences), and the tubes were centrifuged using a centrifuge at room temperature and 950 G for 30 minutes. After centrifugation, lymphocytes present in the intermediate layer between the Ficoll-Paque and the supernatant were recovered, and suspended in a D-PBS solution containing 3% fetal calf serum (FCS: JRH Biosiences) and 2 mM EDTA (Dojindo Inc) (hereinafter, referred to as MACS buffer); the suspension was centrifuged using a centrifuge at 4° C. and 500 G for 5 minutes to sediment the lymphocytes. The resulting lymphocyte pellet was again suspended in MACS buffer; the suspension was centrifuged at 500 G for 5 minutes to sediment the lymphocytes, and twice washed to yield a lymphocyte pellet. This cell pellet was again suspended in the MACS buffer to obtain a cell density of $1 \times 10^8$ cells/ml. To $1 \times 10^7$ lymphocytes, 2 µL of an FITC-labeled anti-human CD8 antibody (BD BioScience Pharmingen) and 2 µL of an FITC-labeled anti-human CD45RO antibody (BD BioScience Pharmingen) were added, and they were reacted on ice for 30 minutes to thereby bind each antibody. The MACS buffer was added to the reaction mixture, and the mixture was centrifuged and twice washed at 4° C. Next, 10 µL of anti-FITC microbeads (Miltenyi Biotec GmbH) was added to $1 \times 10^7$ lymphocytes coupled with each antibody, and they were reacted with each other on ice for 15 minutes. The MACS buffer was added to the reaction mixture, and the mixture was centrifuged and twice washed at 4° C. The cell pellet obtained was suspended in the MACS buffer to obtain a cell density of $5 \times 10^7$/ml, and the suspension was passed through a nylon mesh (Abe Kagaku), after which a CD8- and CD45RO-double-negative fraction was recovered using an automated magnetic cell sorter (AutoMACS Miltenyi Biotec GmbH) to thereby separate human naive CD4T cells, which were supplied for the following experiments.

1.6. In Vitro T Cell Differentiation Culture

Naive CD4T cells separated from human peripheral blood were sown to a culture plate under Th1 differentiation conditions to obtain a cell density of $5 \times 10^5$ cells/0.5 ml/well, and stimulated and cultured under the following conditions. Th1/2 stimulation and subsequent cultivation were performed using a $CO_2$ incubator in the presence of 5% $CO_2$ at 37° C. Under Th1 differentiation conditions, 50 U/ml (final concentration) IL-2 (Immunace, Shionogi & Co., Ltd.), 1 ng/ml (final concentration) IL-12 (PeproTech), and 5 µg/ml (final concentration) anti-IL-4 antibody (Pharmingen) were added to an RPMI-1640 medium (SIGMA) containing 10% fetal calf serum (FCS: JRH Biosiences), 10 mM HEPES (GIBCO), 100 µM Non-Essential Amino Acids (GIBCO), 1 mM Sodium Pyruvate (GIBCO), and 55 µM 2-Mercaptoethanol (GIBCO) (hereinafter called differentiation induction medium). In a flat-bottomed 48-well tissue culture plate (Coaster) having 20 µg/ml of an anti-CD3 antibody (ORTHO-CLONE OKT3, Janssen Pharmaceutical K.K.) immobilized thereon, the cells were cultured for 2 days. Furthermore, the cells were transferred to a non-immobilization plate without the anti-CD3 antibody, and further cultured under Th1 differentiation culture conditions without the anti-IL-4 antibody for 5 days.

Under Th2 differentiation conditions, the cells were stimulated on a plate having the anti-CD3 antibody immobilized thereon for 2 days in a differentiation induction medium containing 50 U/ml (final concentration) IL-2 (Immunace, Shionogi & Co., Ltd.), 1 ng/ml (final concentration) IL-4, and 5 µg/ml (final concentration) anti-IFNγ antibody (Pharmingen, and the cells were transferred to a plate without immobilized anti-CD3 antibody, and cultured for 5 days. Furthermore, in the case of Th2 cell differentiation, following the 2 days, 5 days of differentiation induction was performed in two consecutive cycles.

Unless otherwise specified, the final concentrations of CW, LAM/LM, $PIM_2$ and $PIM_6$ were adjusted to 100 µg/ml.

1.7. Intracellular Staining of IL-4 and IFNγ, and Flowcytometric Analysis

Intracellular staining of IL-4 and IFNγ was performed as described (Proc. Natl. Acad. Sci. USA, 96, 1024 (1999)).

Cells undergoing Th1 differentiation induction (Th1-induced cells) and cells undergoing Th2 differentiation induction (Th2-induced cells) were cultured and stimulated in the presence of Monensin (Sigma) in a medium supplemented with PMA (Phorbol-12-Myristate-13-Acetate, Sigma-Aldrich) and Ionomycin (Calbiochem) for 4 hours. After stimulation, intracellular staining was performed by the method described below, the cells were analyzed using a cell analyzer (FACScalibur), and the degree of Th1 or Th2 differentiation induction was evaluated.

In detail, Th1-induced cells or Th2-induced cells were sown to a flat-bottomed 48-well tissue culture plate to obtain a cell density of $5-10 \times 10^5$ cells per well, 10 ng/ml (final concentration) PMA and 1 µM (final concentration) Ionomycin were added in the presence of 2 µM Monensin, and the cells were cultured and stimulated at 37° C. in the presence of 5% $CO_2$ for 4 hours. The cells were fixed with 4% paraformaldehyde at room temperature for 10 minutes, and permeabilized with 0.5% Triton X-100 (in 50 mM NaCl, 5 mM EDTA and 0.02% $NaN_3$, pH 7.5) on ice for 10 minutes. After blocking with a PBS containing 3% BSA for 15 minutes, the cells were intracellularly stained using a PE-labeled anti-human IL-4 antibody (IL-4 PE) and a FITC-labeled anti-human IFNγ antibody (IFNγ-FITC) (Becton-Dickinson), and the amount of IL-4 or IFNγ cytokine in the cells was evaluated. Concurrently, the cells were stained with an APC-labeled anti-human CD4 antibody (CD4 APC) (BD Biosciences), and examined using a cell analyzer (FACScalibur). Analysis was performed using CellQuest software (Becton Dickinson), for only CD4-expressing T cells gated.

1.8. Preparation of Purified Naive CD4T Cells and Monocyte-Derived Dendritic Cells (moDC)

Purified naive CD4T cells ($CD4^+$, $CD45RA^+$) were purified using a kit for isolation of naive CD4T cells (Mylteni Biotec Inc.) and the AutoMACS sorter. The purity ($CD4^+$, $CD45RA^+$) exceeded 95%.

To prepare moDCs, all PBMCs were allowed to adhere to a culture flask at 37° C. for 1.5-2 hours, and the resulting adhesive cells were cultured in the presence of rhIL-4 (500 U/ml, R&D Systems) and rhGM-CSF (800 U/ml) for 5 to 7 days (International Journal of Cancer, Volume 117, Issue 2, Pages 265-273, 2005). $CD11c^+$ cells were purified using a MACS separation column (Miltenyi Biotech) according to the manufacturer's protocol. The cells obtained were used in in vitro T cell differentiation culture, and the involvement of DC was examined.

1.9. Effects of LAM/LM, CW, $Ac_4PIM_2$, $Ac_3PIM_2$, $Ac_4PIM_6$ and Cardiolipin in a Human Th1/Th2 Differentiation Induction System Using Naive T Cells Using naive T cells separated and prepared from human peripheral blood, under conditions with the addition of LAM/LM, CW, $Ac_4PIM_2$, $Ac_3PIM_2$, $Ac_4PIM_6$ or cardiolipin, Th1 differentiation induction or Th2 differentiation induction was performed using the above-described Th1/Th2 differentiation induction system, and an evaluation was made to determine whether or not LAM/LM, CW, $Ac_4PIM_2$, $Ac_3PIM_2$, $Ac_4PIM_6$, and cardiolipin modify Th1 induction or Th2 induction.

In detail, naive CD4T cells separated from human peripheral blood were sown to a culture plate under Th1 differentiation conditions to obtain a cell density of $5\times10^5$ cells/0.5 ml/well, and stimulated and cultured under the conditions shown below. Th1 or Th2 stimulation and subsequent cultivation were performed using a $CO_2$ incubator in the presence of 5% $CO_2$ at 37° C. Under Th1 differentiation conditions, 50 U/ml (final concentration) IL-2 (Immunace, Shionogi & Co., Ltd.), 1 ng/ml (final concentration) IL-12 (PeproTech), and 5 µg/ml (final concentration) anti-IL-4 antibody (Pharmingen) were added to a differentiation induction medium. Furthermore, LAM/LM, CW, $Ac_4PIM_2$, $Ac_3PIM_2$, $Ac_4PIM_6$, and cardiolipin were added to respective wells to obtain a cell density of 100 µg/ml, and cultured in a flat-bottomed 48-well tissue culture plate (Coaster) having 20 µg/ml of an anti-CD3 antibody (ORTHOCLONE OKT3, Janssen Pharmaceutical K.K.) immobilized thereon for 2 days. Furthermore, the cells were transferred to a plate without immobilized anti-CD3 antibody, and further cultured under Th1 differentiation culture conditions without the anti-IL-4 antibody for 5 days.

Under the Th2 differentiation conditions, naive T cells were sown to a culture plate to obtain a cell density of $5\times10^5$ cells/0.5 ml/well, and stimulated under the conditions shown below. Specifically, using a differentiation induction medium containing 50 U/ml (final concentration) IL-2 (Immunace, Shionogi & Co., Ltd.), 1 ng/ml (final concentration) IL-4, and 5 µg/ml (final concentration) anti-IFNγ antibody (Pharmingen), LAM/LM, CW, $Ac_4PIM_2$, $Ac_3PIM_2$, $Ac_4PIM_6$, and cardiolipin were added to respective wells to obtain a concentration of 100 µg/ml, the cells were stimulated in a plate having an anti-CD3 antibody immobilized thereon for 2 days, and the cells were transferred to a plate without immobilized anti-CD3 antibody and cultured for 5 days. Furthermore, in the case of Th2 cell differentiation, following the 2 days, 5 days of differentiation induction was performed in two consecutive cycles.

Under conditions with the addition of LAM/LM, CW, $AC_4PIM_2$, $AC_3PIM_2$, $AC_4PIM_6$, and cardiolipin, cells undergoing Th1 differentiation induction or Th2 differentiation induction were cultured and stimulated in the presence of Monensin (Sigma) in a medium supplemented with PMA (Phorbol-12-Myristate-13-Acetate, Sigma-Aldrich) and Ionomycin (Calbiochem) for 4 hours. After stimulation, intracellular staining was performed by the method described below, and the cells were analyzed using a cell analyzer (FACScalibur), and the degree of Th1 or Th2 differentiation induction was evaluated.

In detail, Th1-induced cells or Th2-induced cells were sown to a flat-bottomed 48-well tissue culture plate to obtain a density of $5-10\times10^5$ cells per well, 10 ng/ml (final concentration) PMA and 1 µM (final concentration) Ionomycin were added in the presence of 2 µM Monensin, and the cells were cultured and stimulated at 37° C. in the presence of 5% $CO_2$ for 4 hours. The cells were intracellularly stained with a PE-labeled anti-human IL-4 antibody and a FITC-labeled anti-human IFNγ antibody (Becton-Dickinson), and the amount of IL-4 or IFNγ cytokine accumulated in the cells were evaluated. Concurrently, the cells were stained with an APC-labeled anti-human CD4 antibody (CD4 APC) (BD Biosciences), and measured using a cell analyzer (FACScalibur). Analysis was performed using CellQuest software (Becton Dickinson), for only CD4-expressing T cells gated.

2. Results 2.1. BCG Crude Cell Wall Fraction (BCG-CCW)

The particle size distribution in the prepared BCG-CCW is shown in FIG. 1. From electron microscopic images, it is confirmed that most of the BCG cell bodies had been homogenized by French press treatment. Regarding the particle size distribution in each fraction, CW had a median diameter of about 240 nm, and CM had a median diameter of about 130 nm (FIG. 1).

2.2. BCG Cell Body Phospholipids

Figure 2:
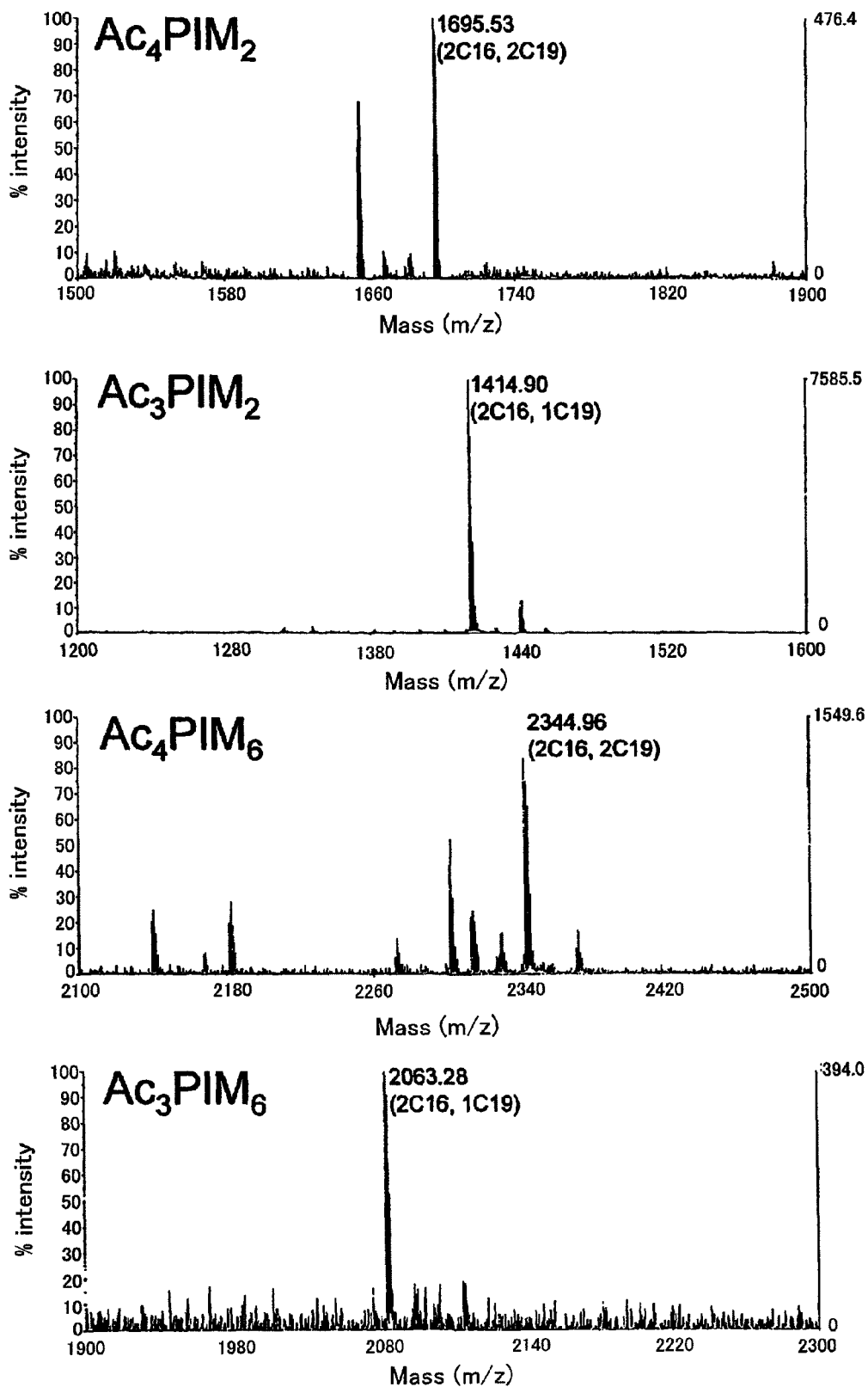
FIG. 2 shows MALDI-TOF mass spectra of PIMs isolated from BCG cell bodies.

Cardiolipin and several kinds of PIM were isolated and purified as phospholipids from the whole lipid of BCG cell bodies. The PIMx were subjected to MALDI-TOF Mass determination; as a result, from the molecular ion peaks and fragment ions, the PIMx were identified to be $Ac_4PIM_2$, $Ac_3PIM_2$, $Ac_4PIM_6$ and $Ac_3PIM_6$ (FIG. 2).

2.3. LAM and LM

Figure 3:
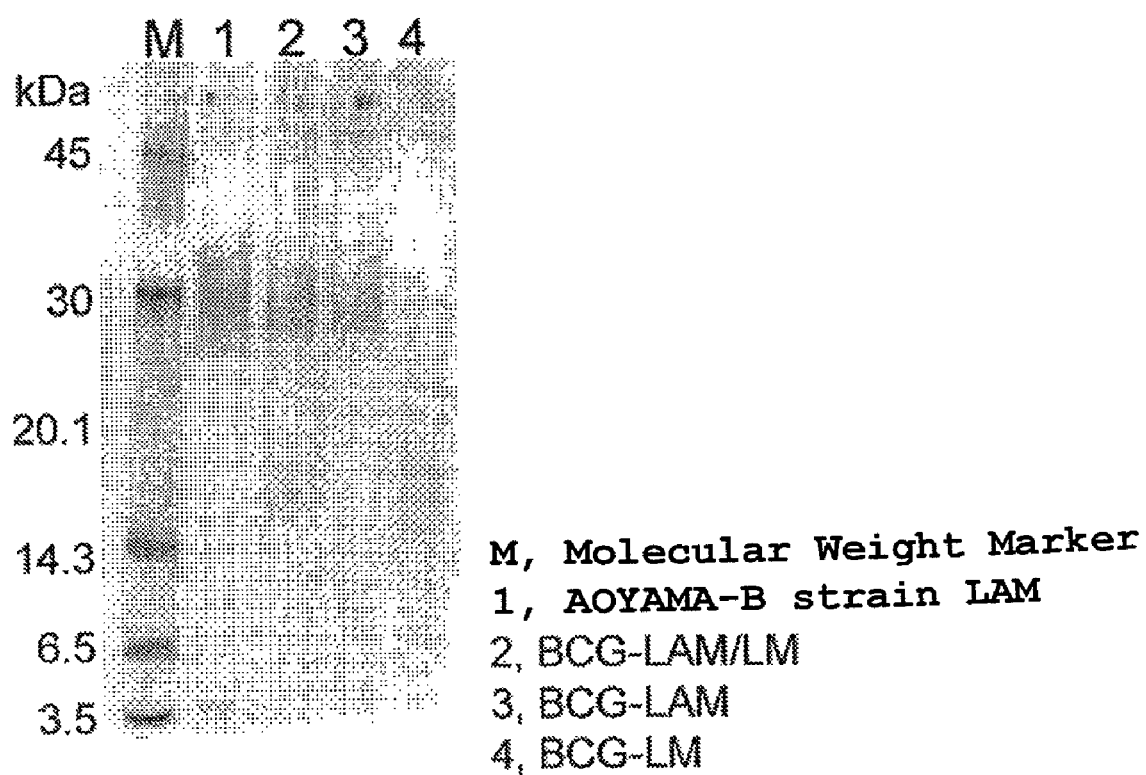
FIG. 3 shows SDS-PAGE analyses of isolated BCG-LAM and -LM.
Figure 4:
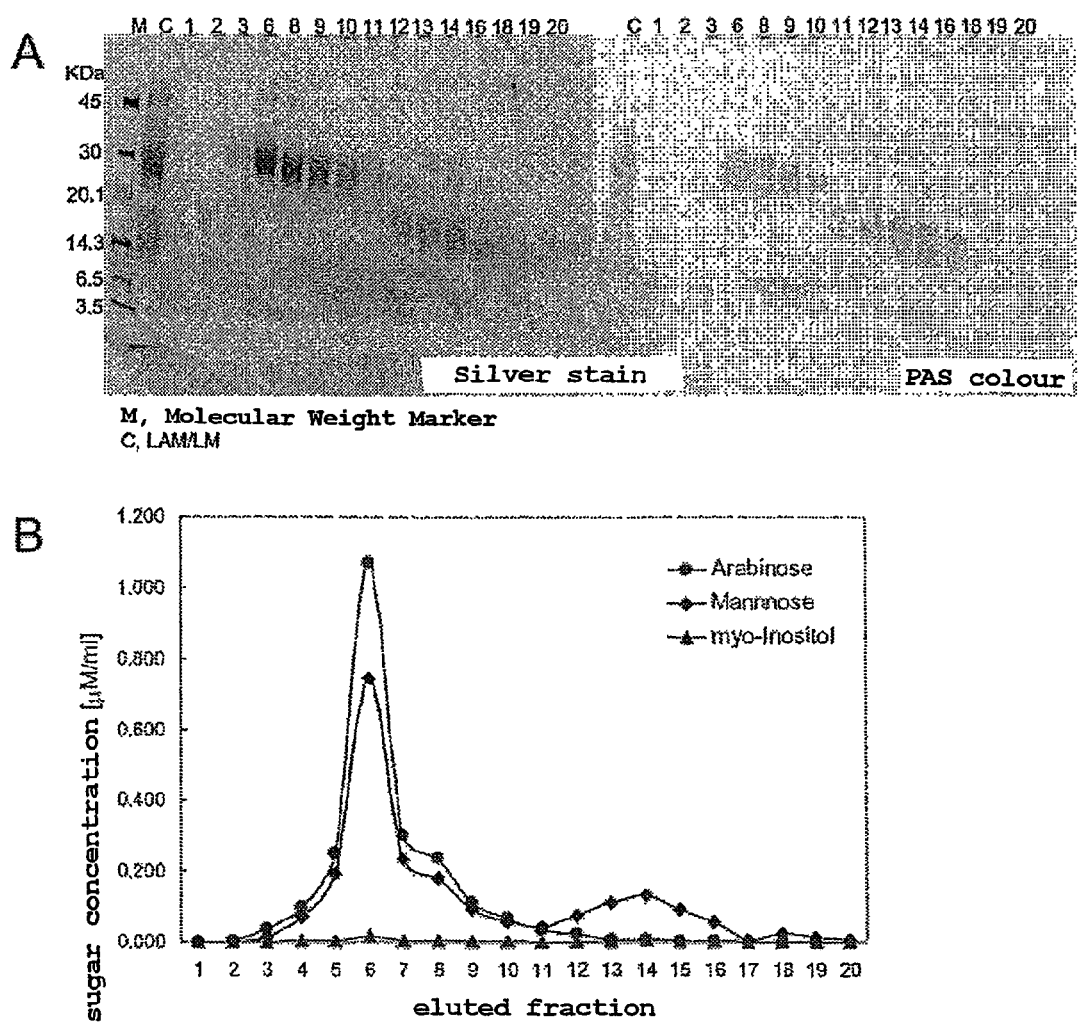
FIG. 4 shows the fractionation of BCG-LAM and -LM by gel filtration chromatography. (A) SDS-PAGE analysis of eluted fractions of LAM or LM. (B) Measurements of the mannose, arabinose and myo-innositol contents of each eluted fraction by GC/MS.

BCG-LM was eluted slightly more slowly than BCG-LAM in gel filtration chromatography (FIG. 4A). Furthermore, the mannose, arabinose and myo-innositol contents of each eluted fraction were quantified by GC/MS (FIG. 4B). In SDS-PAGE, BCG-LAM exhibited nearly the same Rf value as LAM derived from the M. tuberculosis AOYAMA-B strain (FIG. 3).

2.4. MALDI-TOF Mass Analysis

Figure 5:
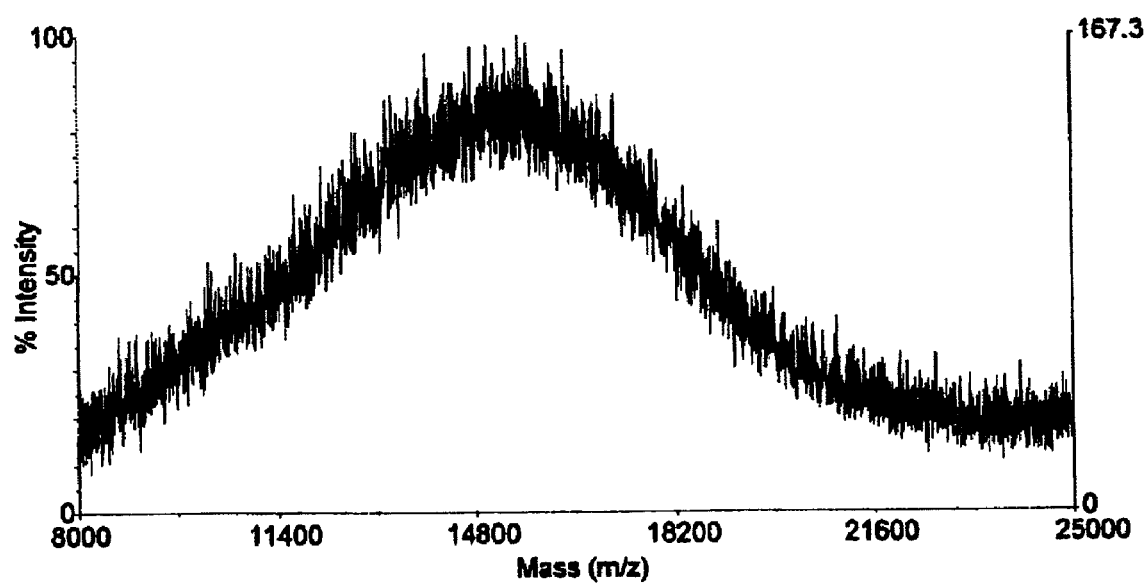
FIG. 5 shows a MALDI-TOF mass spectrum of BCG-LAM.

In M. tuberculosis AOYAMA-B LAM, deprotonated molecular ions $[M-H]^-$ are distributed in the wide range of m/z 13000 to m/z 19500, centering at m/z 17000; in BCG Tokyo 172-LAM, the ions were detected in the range of m/z 13000 to m/z 17000, centering at a slightly lower molecular weight of m/z 15000, suggesting a difference in sugar residue content (FIG. 5). In BCG Tokyo 172-LM, unlike in LAM, deprotonated molecular ions [M-H]⁻ were detected distinctly, and it was proved to be a tri-acyl (2C16, C19) LM consisting mainly of 20 to 48 mannose units (m/z 4500 to m/z 9000) (FIG. 6A). In mass spectrometry of the deacylated form of BCG Tokyo 172-LM, a still distinct deprotonated molecular ions [M-H]⁻ were detected (FIG. 6B).

2.5. Fatty Acid Analysis of LAM, LM and PIM

Furthermore, the constituent fatty acid compositions of these LAM, LM and PIM were analyzed by GC and GC/MS after methyl-esterification; for all of LAM, LM and PIM, the major fatty acids were palmitic acid (C16:0), stearic acid (C18:0) and tuberculostearic acid (10-methyl C18:0), which accounted for 90% or more (Table 1).

TABLE 1

| Fatty acids (%) | LAM | LM | PIM |
| --- | --- | --- | --- |
| C14:0 | 0.1 | 0.1 | 0.1 |
| C15:0 | 0.0 | 0.1 | 0.1 |
| C16:0 | 39.4 | 44.2 | 44.5 |
| br C17:0 | 4.1 | 5.6 | 4.4 |
| C17:0 | 0.8 | 0.6 | 0.8 |
| br C18:0 | 0.0 | 0.0 | 0.0 |
| cis C18:1[9] | 3.4 | 2.7 | 2.5 |
| C18:0 | 19.9 | 10.6 | 12.2 |
| 10-methyl C18:0 | 32.3 | 36.1 | 35.4 |
| Total | 100 | 100 | 100 |

2.6. Partially Methylated Alditol Acetate Analysis of LAM and LM

To clarify the branched structures of the sugar chains of the above-described LAM, LM (and PIM), partially methylated alditol acetate derivatives were prepared, and GC/MS measurement were performed. In LM, terminal mannose (t-Manp) accounted for 36.6%, 2,6-mannose (2,6-Manp) accounted for 37.6%, 6-mannose (6-Manp) accounted for 18.6%, and 2-mannose (2-Manp) accounted for 7.1%, with an extremely small amount of terminal arabinose contained. In contrast, in LAM, 5-Araf was present at 39.4%, and branched 3,5-Araf was present at 11.8% (Table 2).

TABLE 2

| Abbreviation for glycosyl group[a] | LM Tokyo 172 mol (%) | LAM Tokyo 172 |
| --- | --- | --- |
| t-Araf | 0.1 | 0.4 |
| 2-Araf | | 4.8 |
| 5-Araf | | 39.4 |
| 3,5-Araf | | 11.8 |
| t-Manp | 36.6 | 16.5 |
| 2-Manp | 7.1 | 8.0 |
| 6-Manp | 18.6 | 7.0 |
| 2,6-Manp | 37.6 | 12.1 |

The abbreviations in the table above are defined below:
t-Araf, 2,3,5-tri-O-Me-1,4-di-O-Ac-arabinitol;
2-Araf, 3,5-di-O-Me-1,2,4-tri-O-Ac-arabinitol;
5-Araf, 2,3-di-O-Me-1,4,5-tri-O-Ac-arabinitol;
3,5-Araf, 2-O-Me-1,3,4,5-tetra-O-Ac-arabinitol;
t-Manp, 2,3,4,6-tetra-O-Me-1,5-di-O-Ac-mannitol;
2-Manp, 3,4,6-tri-O-Me-1,2,5-tri-O-Ac-mannitol;
6-Manp, 2,3,4-tri-O-Me-1,5,6-tri-O-Ac-mannitol;
2,6-Manp, 3,4-di-O-Me-1,2,5,6-tetra-O-Ac-mannitol 2.7. Identification of Subclasses and Molecular Species of BCG Tokyo 172-LM The mass numbers of molecular species Man 2 to 50 of BCG Tokyo 172-LM are shown in Table 3. Table 3 shows the mass numbers of various subclasses of BCG Tokyo 172-LM by fatty acid (acyl group) number subclass and molecular species composition.

TABLE 3

| Nunber of mannnose in LM | Deprotonated molecule [M-H]⁻ of LM | | | | | | | | | |
| --- | --- | --- | --- | --- | --- | --- | --- | --- | --- | --- |
| | mono-acyl LM | | | di-acyl LM | | | tri-acyl LM | | tri-acyl mono-Ara LM | |
| | (C16) | (C18) | (C19) | (2C16) | (C16, C18) | (C16, C19) | (2C16, C19) | (C16, C18, C19) | (2C16, C19) | (C16, C18, C19) |
| 2 | 895.9 | 924.0 | 938.0 | 1134.3 | 1162.4 | 1176.4 | 1414.8 | 1442.8 | 1546.9 | 1575.0 |
| 4 | 1220.2 | 1248.2 | 1262.3 | 1458.6 | 1486.6 | 1500.7 | 1739.1 | 1767.1 | 1871.2 | 1899.2 |
| 6 | 1544.5 | 1572.5 | 1586.5 | 1782.9 | 1810.9 | 1824.9 | 2063.4 | 2091.4 | 2195.5 | 2223.5 |
| 8 | 1868.7 | 1896.8 | 1910.8 | 2107.1 | 2135.2 | 2149.2 | 2387.6 | 2415.7 | 2519.8 | 2547.8 |
| 10 | 2193.0 | 2221.1 | 2235.1 | 2431.4 | 2459.5 | 2473.5 | 2711.9 | 2740.0 | 2844.0 | 2872.1 |
| 12 | 2517.3 | 2545.4 | 2559.4 | 2755.7 | 2783.8 | 2797.8 | 3036.2 | 3064.3 | 3168.3 | 3196.4 |
| 14 | 2841.6 | 2869.6 | 2883.7 | 3080.0 | 3108.0 | 3122.1 | 3360.5 | 3388.5 | 3492.6 | 3520.6 |
| 16 | 3165.9 | 3193.9 | 3207.9 | 3404.3 | 3432.3 | 3446.2 | 3684.8 | 3712.8 | 3816.9 | 3844.9 |
| 18 | 3490.1 | 3518.2 | 3532.2 | 3728.6 | 3756.6 | 3770.6 | 4009.0 | 4037.1 | 4141.2 | 4169.2 |
| 20 | 3814.4 | 3842.5 | 3856.5 | 4052.8 | 4080.9 | 4094.9 | 4333.3 | 4361.4 | 4465.4 | 4493.5 |
| 21 | 3976.6 | 4004.6 | 4018.6 | 4215.0 | 4243.0 | 4257.1 | 4495.5 | 4523.5 | 4627.6 | 4655.6 |
| 22 | 4138.7 | 4166.8 | 4180.8 | 4377.1 | 4405.2 | 4419.2 | 4657.6 | 4685.7 | 4789.7 | 4817.8 |
| 23 | 4300.8 | 4328.9 | 4342.9 | 4539.3 | 4567.3 | 4581.3 | 4819.7 | 4847.8 | 4951.9 | 4979.9 |
| 24 | 4463.0 | 4491.0 | 4505.1 | 4701.4 | 4729.5 | 4743.5 | 4981.9 | 5009.9 | 5114.0 | 5142.1 |
| 25 | 4625.1 | 4653.2 | 4667.2 | 4863.5 | 4891.6 | 4905.6 | 5144.0 | 5172.1 | 5276.1 | 5304.2 |
| 26 | 4787.3 | 4815.3 | 4829.4 | 5025.7 | 5053.7 | 5067.8 | 5306.2 | 5334.2 | 5438.3 | 5466.3 |
| 27 | 4949.4 | 4977.5 | 4991.5 | 5187.8 | 5215.9 | 5229.9 | 5468.3 | 5496.4 | 5600.4 | 5628.5 |
| 28 | 5111.6 | 5139.6 | 5153.6 | 5350.0 | 5378.0 | 5392.0 | 5630.4 | 5658.5 | 5762.6 | 5790.6 |
| 29 | 5273.7 | 5301.7 | 5315.8 | 5512.1 | 5540.2 | 5554.2 | 5792.6 | 5820.6 | 5924.7 | 5952.8 |
| 30 | 5435.8 | 5463.9 | 5477.9 | 5674.2 | 5702.3 | 5716.3 | 5954.7 | 5982.8 | 6086.8 | 6114.9 |
| 31 | 5598.0 | 5626.0 | 5640.1 | 5836.4 | 5864.4 | 5878.5 | 6116.9 | 6144.9 | 6249.0 | 6277.0 |
| 32 | 5760.1 | 5788.2 | 5802.2 | 5998.5 | 6026.6 | 6040.6 | 6279.0 | 6307.1 | 6411.1 | 6439.2 |
| 33 | 5922.3 | 5950.3 | 5964.3 | 6160.7 | 6188.7 | 6202.7 | 6441.2 | 6469.2 | 6573.3 | 6601.3 |
| 34 | 6084.4 | 6112.4 | 6126.5 | 6322.8 | 6350.9 | 6364.9 | 6603.3 | 6631.3 | 6735.4 | 6763.5 |
| 35 | 6246.5 | 6274.6 | 6288.6 | 6484.9 | 6513.0 | 6527.0 | 6765.4 | 6793.5 | 6897.5 | 6925.6 |
| 36 | 6408.7 | 6436.7 | 6450.8 | 6647.1 | 6675.1 | 6689.2 | 6927.6 | 6955.6 | 7059.7 | 7087.7 |
| 37 | 6570.8 | 6598.9 | 6612.9 | 6809.2 | 6837.3 | 6851.3 | 7089.7 | 7117.8 | 7221.8 | 7249.9 |
| 38 | 6733.0 | 6761.0 | 6775.0 | 6971.4 | 6999.4 | 7013.4 | 7251.9 | 7279.9 | 7384.0 | 7412.0 |

TABLE 3-continued

| Number of mannnose in LM | Deprotonated molecule [M-H]⁻ of LM | | | | | | | | | |
|---|---|---|---|---|---|---|---|---|---|---|
| | mono-acyl LM | | | di-acyl LM | | | tri-acyl LM | | tri-acyl mono-Ara LM | |
| | (C16) | (C18) | (C19) | (2C16) | (C16, C18) | (C16, C19) | (2C16, C19) | (C16, C18, C19) | (2C16, C19) | (C16, C18, C19) |
| 39 | 6895.1 | 6923.2 | 6937.2 | 7133.5 | 7161.6 | 7175.6 | 7414.0 | 7442.0 | 7546.1 | 7574.2 |
| 40 | 7057.2 | 7085.3 | 7099.3 | 7295.6 | 7323.7 | 7337.7 | 7576.1 | 7604.2 | 7708.3 | 7736.3 |
| 41 | 7219.4 | 7247.4 | 7261.5 | 7457.8 | 7485.8 | 7499.9 | 7738.3 | 7766.3 | 7870.4 | 7898.4 |
| 42 | 7381.5 | 7409.6 | 7423.6 | 7619.9 | 7648.0 | 7662.0 | 7900.4 | 7928.5 | 8032.5 | 8060.6 |
| 43 | 7543.7 | 7571.7 | 7585.7 | 7782.1 | 7810.1 | 7824.2 | 8062.6 | 8090.6 | 8194.7 | 8222.7 |
| 44 | 7705.8 | 7733.9 | 7747.9 | 7944.2 | 7972.3 | 7986.3 | 8224.7 | 8252.8 | 8356.8 | 8384.9 |
| 45 | 7867.9 | 7896.0 | 7910.0 | 8106.4 | 8134.4 | 8148.4 | 8386.8 | 8414.9 | 8519.0 | 8547.0 |
| 46 | 8030.1 | 8058.1 | 8072.2 | 8268.5 | 8296.5 | 8310.6 | 8549.0 | 8577.0 | 8681.1 | 8709.1 |
| 47 | 8192.2 | 8220.3 | 8234.3 | 8430.6 | 8458.7 | 8472.7 | 8711.1 | 8739.2 | 8843.2 | 8871.3 |
| 48 | 8354.4 | 8382.4 | 8396.4 | 8592.8 | 8620.8 | 8634.9 | 8873.3 | 8901.3 | 9005.4 | 9033.4 |
| 49 | 8516.5 | 8544.6 | 8558.6 | 8754.9 | 8783.0 | 8797.0 | 9035.4 | 9063.5 | 9167.5 | 9195.6 |
| 50 | 8678.6 | 8706.7 | 8720.7 | 8917.1 | 8945.1 | 8959.1 | 9197.5 | 9225.6 | 9329.7 | 9357.7 |

The structure of the major LM contained in BCG Tokyo 172, determined from the results shown above, is shown by the formula:

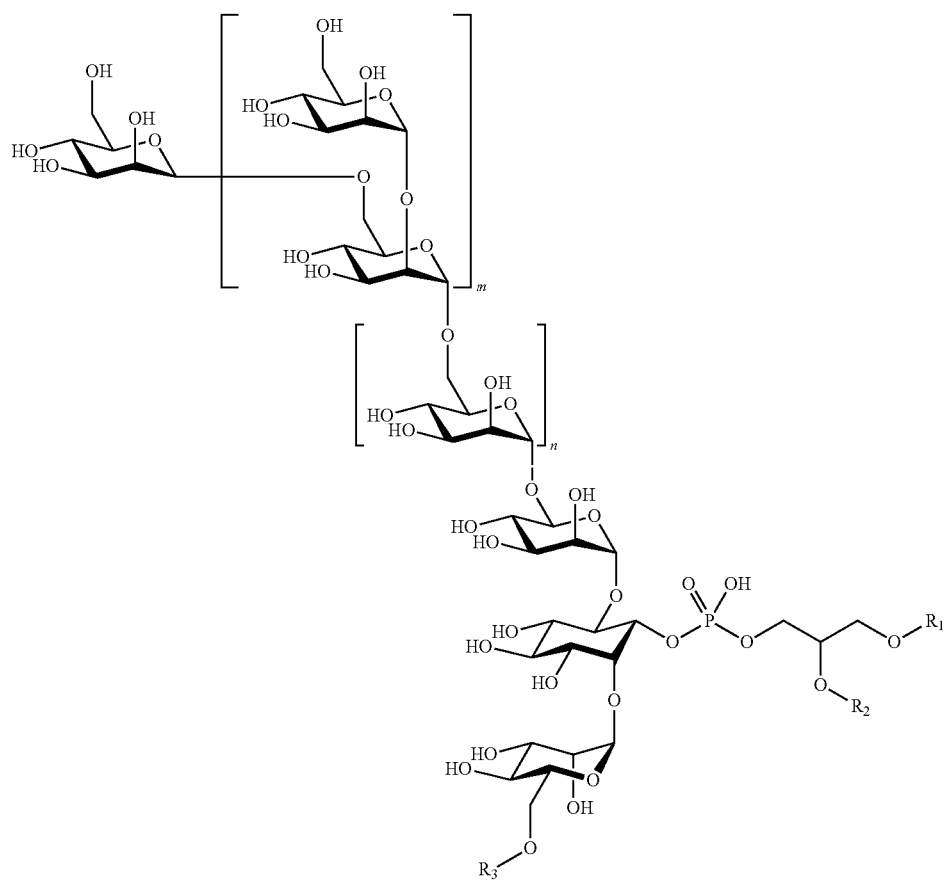

(wherein $R_1$ is an acyl group derived from tuberculostearic acid, each of $R_2$ and $R_3$ is an acyl group derived from palmitic acid, m indicates an integer of 1 to 22, n indicates an integer of 1 to 10, and 20 to 48 mannose residues are contained).

Using the thus purified LAM, LM, or a mixture thereof (crude LAM/LM), the effects of these molecules on Th1/Th2 differentiation induction were examined.

2.8. Induction of IFNγ-Producing Cells by LAM/LM

Figure 7:
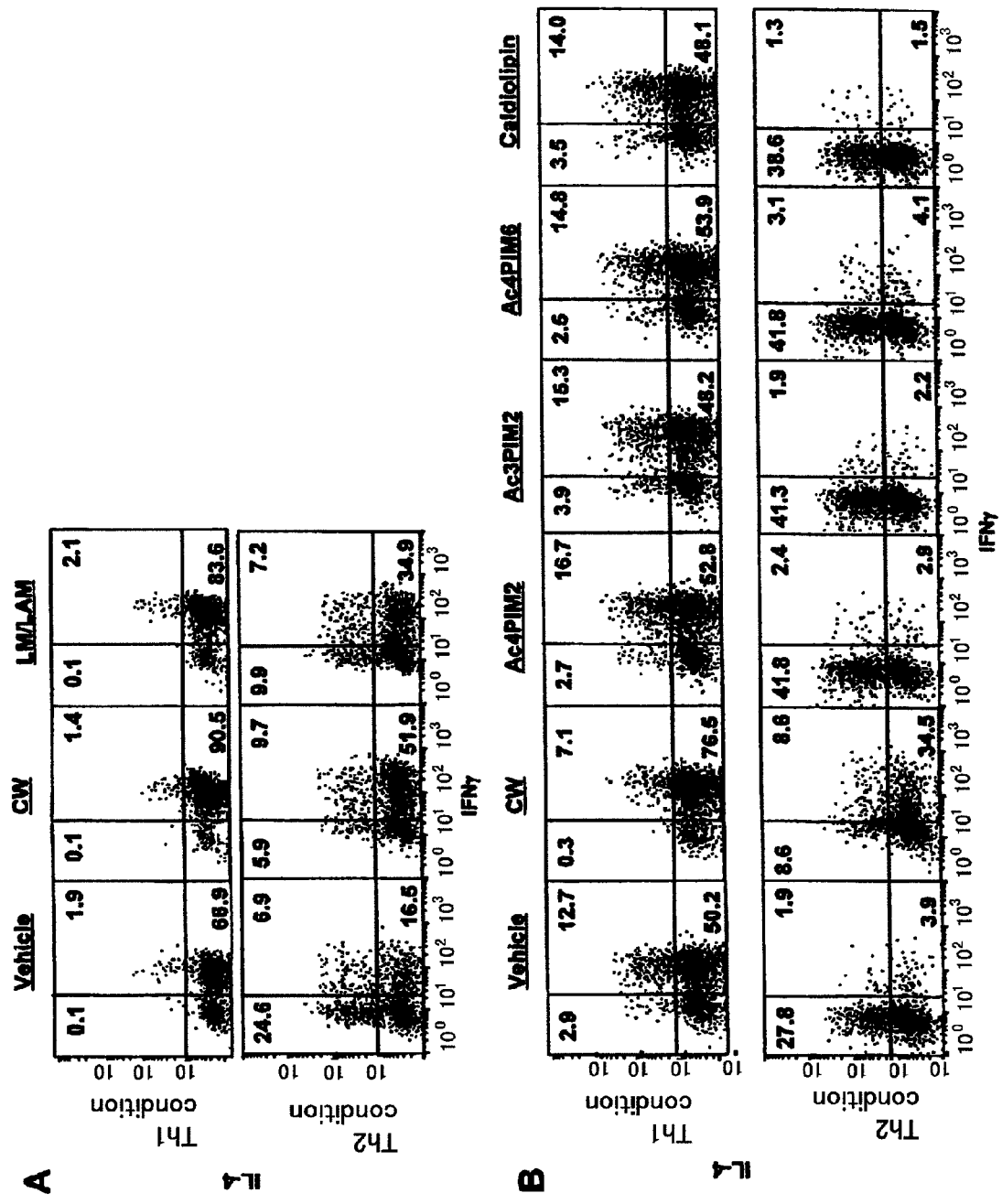
FIG. 7 shows the induction of IFNγ-producing cells by BCG-related products in human PBMC Th1/Th2 differentiation culture. A and B show the results of independent tests. The numerical figures in the gates indicate the ratios (%) of cells in the respective gates.

LAM/LM was applied to a system for human Th1/Th2 differentiation induction, and its effect was examined. The solvent (vehicle) for LAM/LM was used for negative control. Furthermore, the cell wall (CW) was used for positive control for Th1 inducing factors. In Th1 differentiation induction, CW increased the ratio of IFNγ-producing cells to 90.5%, and LAM/LM increased the ratio to 83.6% (vehicle: 66.9%). These molecules acted as potent Th1 inducing factors (FIG. 7A). Furthermore, under Th2 differentiation conditions, CW suppressed the ratio of IL-4-producing cells to 5.9% (vehicle: 24.6%) and increased the ratio of IFNγ-producing cells to 51.9% (vehicle: 16.5%). LAM/LM suppressed the ratio of IL-4-producing cells to 9.9% and increased the ratio of IFNγ-producing cells to 34.9% (FIG. 7A). Meanwhile, $Ac_4PIM_2$, $Ac_3PIM_2$, $Ac_4PIM_6$ and cardiolipin, which are precursors of LAM/LM, did not exhibit the potential to induce Th1 differentiation (FIG. 7B). Furthermore, under Th2 differentiation inducing conditions, these molecules did not increase the ratio of IFNγ-producing cells, but increased the ratio of IL-4-producing cells (FIG. 7B).

Figure 9:
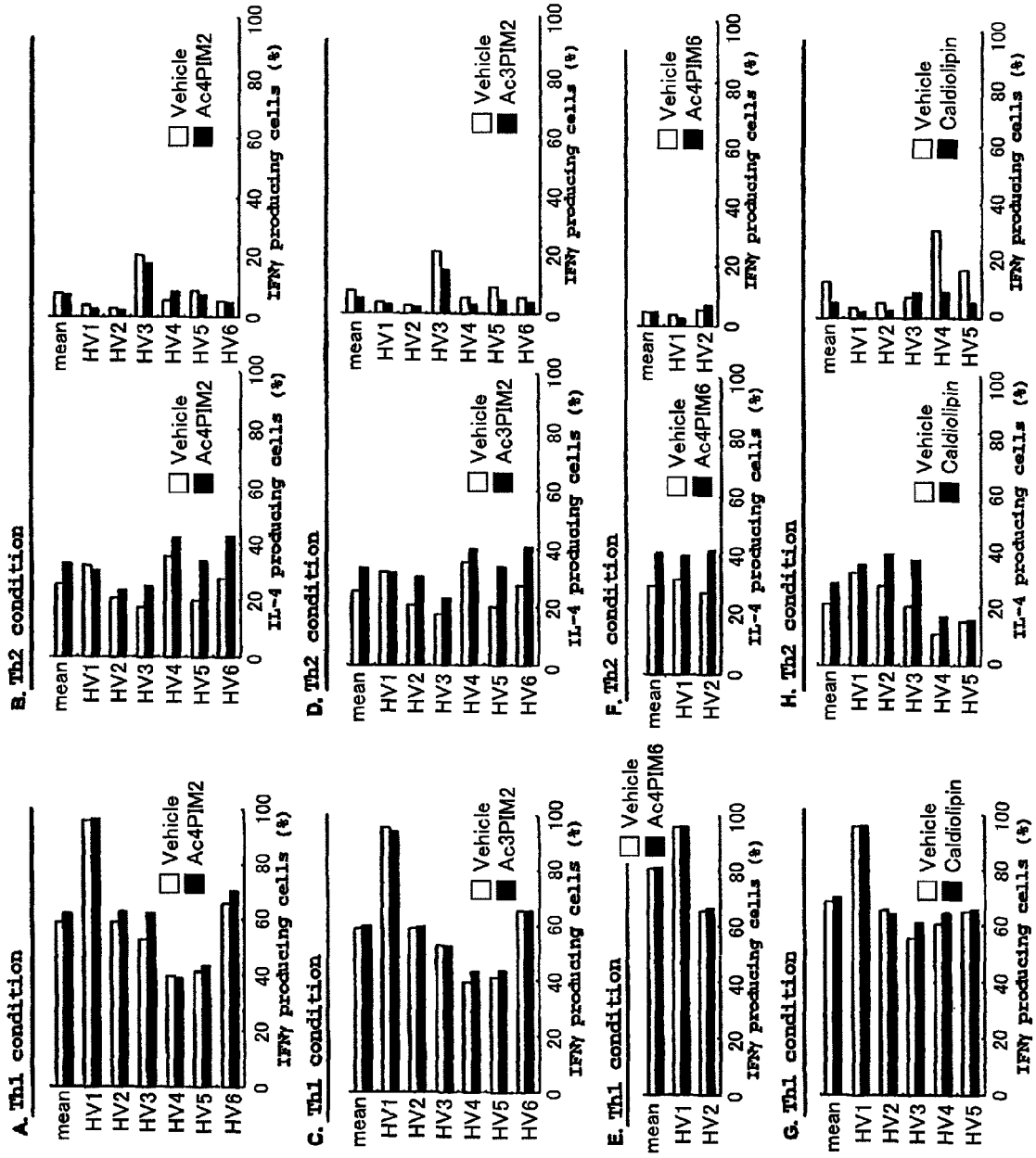
FIG. 9 shows the effects of $Ac_4PIM_2$, $Ac_3PIM_2$, $Ac_4PIM_6$ and cardiolipin on human Th1/Th2 cell differentiation. HV represents each healthy human volunteer. (A) and (B): $Ac_4PIM_2$, (C) and (D): $Ac_3PIM_2$, (E) and (F): $Ac_4PIM_6$(G) and (H): cardiolipin. (A), (C), (E) and (G): Th1 differentiation inducing conditions, (B), (D), (F) and (H): Th2 differentiation inducing conditions.

To confirm these effects, Th1/2 differentiation induction was tested using T cells from six healthy human volunteers. CW increased the number of IFNγ-producing cells under Th1 differentiation conditions in all healthy human volunteers (FIG. 8A). Under Th2 differentiation conditions, CW suppressed the number of IL-4-producing cells and increased the number of IFNγ cells (FIG. 8B). Similar results were obtained with LAM/LM (FIGS. 8C and D). Meanwhile, $Ac_4PIM_2$, $Ac_3PIM_2$, $Ac_4PIM_6$ and cardiolipin did not increase the number of IFNγ-producing cells under Th1 differentiation inducing conditions (FIGS. 9A, C, E and G), and increased the number of IL-4-producing cells under Th2 differentiation inducing conditions (FIGS. 9B, D, F and H). Hence, it was found that LAM/LM is effective in increasing the number of Th1 cells in humans.

2.9. Effects of Dendritic Cells on Human Th1/2 Differentiation

Figure 11:
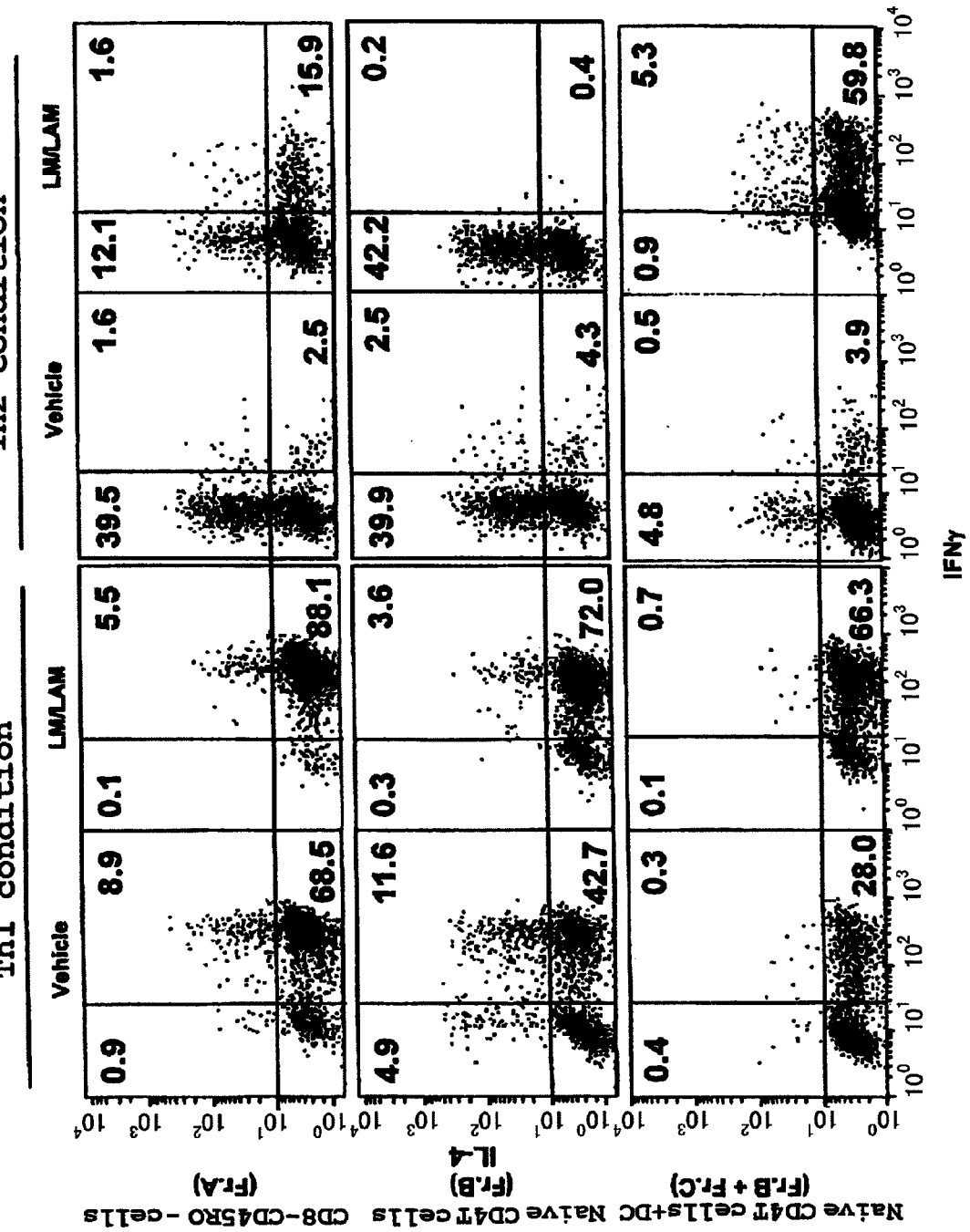
FIG. 11 shows the effects of LAM/LM on human Th1 or Th2 differentiation induction. Tests were performed using $CD8^-CD45RO^-$ cells (FrA) (upper panel), purified CD4T cells (FrB) (middle panel) and purified CD4T cells+dendritic cells (FrB+FrC).

The present inventors examined the involvement of dendritic cells in order to clarify the mechanism for the enhancement of Th1 cell differentiation by LAM/LM.

conditions, with the addition of LAM/LM, the number of IFNγ-producing cells increased to 88.1%, 72.0%, and 66.3% when crude naive CD4 cells (FrA), purified naive CD4 cells (FrB), and purified naive CD4 cells+concentrated DC (FrB+FrC) were used, respectively; in all groups, LAM/LM increased the number of IFNγ-producing cells (FIG. 11). This effect was also observed with the use of FrB or FrB+FrC (FIG. 11). Hence, the increase in the number of IFNγ-producing cells by LAM/LM under Th1 differentiation inducing conditions was observed irrespective of the presence or absence of DC.

Meanwhile, when FrA was used under Th2 differentiation inducing conditions, with the addition of LAM/LM, the number of IL-4-producing cells decreased to 12.1%, and the number of IFNγ-producing cells increased to 15.9%. Meanwhile, when DC-free FrB was used under Th2 differentiation inducing conditions, this effect of LAM/LM was not observed at all. However, with the addition of DC (FrC), the once-lost effect of LAM/LM was restored (FIG. 11). Hence, it was suggested that the increase in the number of IFNγ-producing cells and the reduction in the number of IL-4-producing cells under Th2 differentiation inducing conditions by LAM/LM might be actions mediated by DC (antigen-presenting cells).

2.10. Effects of Purified LAM and LM on Th1/Th2 Differentiation

Purified LAM and LM were applied to a system for Th1/Th2 differentiation induction using crude human CD4T cells, and their effects were examined.

The results of two independent tests under Th1 differentiation inducing conditions are shown in Tables 4 and 5.

TABLE 4

|  | Vehicle | CW (100 μg/ml) | LAM/LM (100 μg/ml) | LM (10 μg/ml) | LM (100 μg/ml) | LAM (10 μg/ml) | LAM (100 μg/ml) |
| --- | --- | --- | --- | --- | --- | --- | --- |
| IFNγ⁺IL-4⁻ cells (%) | 51.2 | 81.1 | 83.5 | 56.7 | 67.9 | 55.9 | 55.4 |

TABLE 5

|  | Vehicle | CW (100 μg/ml) | LAM/LM (100 μg/ml) | LM (30 μg/ml) | LM (100 μg/ml) | LAM (30 μg/ml) | LAM (100 μg/ml) |
| --- | --- | --- | --- | --- | --- | --- | --- |
| IFNγ⁺IL-4⁻ cells (%) | 60.6 | 83.4 | 82.5 | 70.5 | 69.1 | 63.1 | 67.6 |

Figure 10:
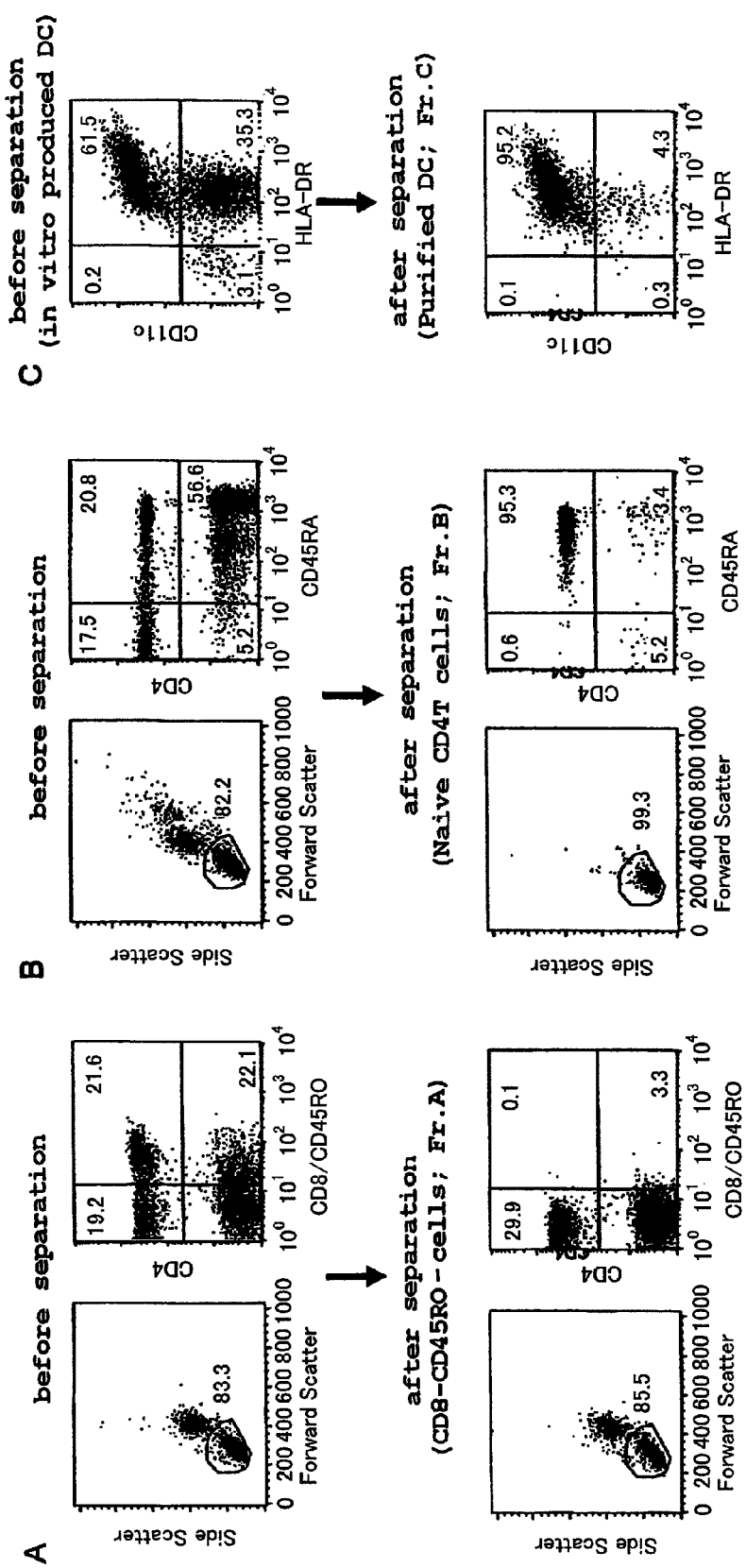
FIG. 10 shows the enrichment of human naive CD4T cells and dendritic cells by AutoMACS. (A) Preparation of crude CD4T cells ($CD8^-CD45RO^-$ cells: FrA). (B) Preparation of purified CD4T cells (FrB). (C) Preparation of dendritic cells (FrC).

Crude naive CD4T cells containing dendritic cells were recovered by removing CD8-CD45RO-positive cells (FIG. 10A). Furthermore, by removing CD8, CD14, CD16, CD19, CD36, CD45RO, CD56, CD123, TCRγδ and Glycophorin-positive cells by AutoMACS, purified naive CD4T cells not containing dendritic cells were recovered (FIG. 10B). To purify dendritic cells, CD11c-negative cells were removed by AutoMACS (FIG. 10C). Thus, crude naive CD4T cells (FrA), purified naive CD4T cells (FrB) and concentrated dendritic cells (FrC) were obtained.

Using these cells in a human Th1/Th2 differentiation culture system, the involvement of dendritic cells in the effects of LAM/LM was examined. Under Th1 differentiation inducing Under Th1 differentiation inducing conditions, each of LAM and LM significantly increased the ratio of IFNγ-producing cells (Tables 4 and 5). This effect was more potent with LM than with LAM. The effect of the LAM/LM mixture was more potent than the effect of LAM or LM alone. Hence, it was demonstrated that LAM and LM enhance the induction of IFNγ-producing cells in Th1 differentiation induction when used alone, and that by mixing LAM and LM, their effects to induce IFNγ-producing cells are synergistically enhanced.

Figure 12:
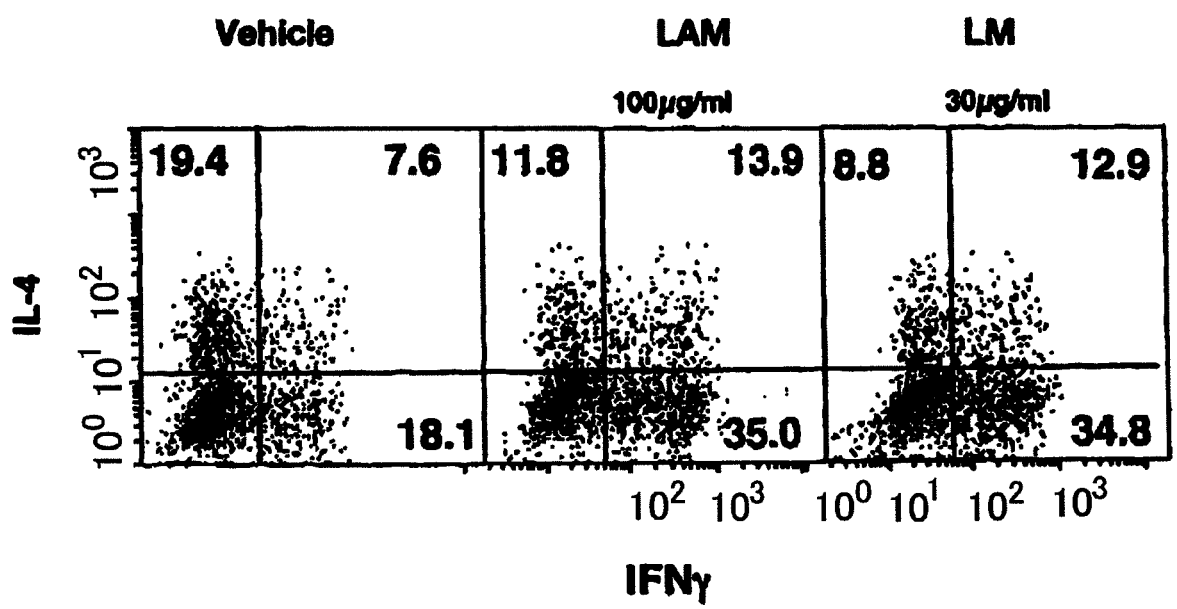
FIG. 12 shows the effects of LAM and LM under Th2 differentiation inducing conditions.
Figure 13:
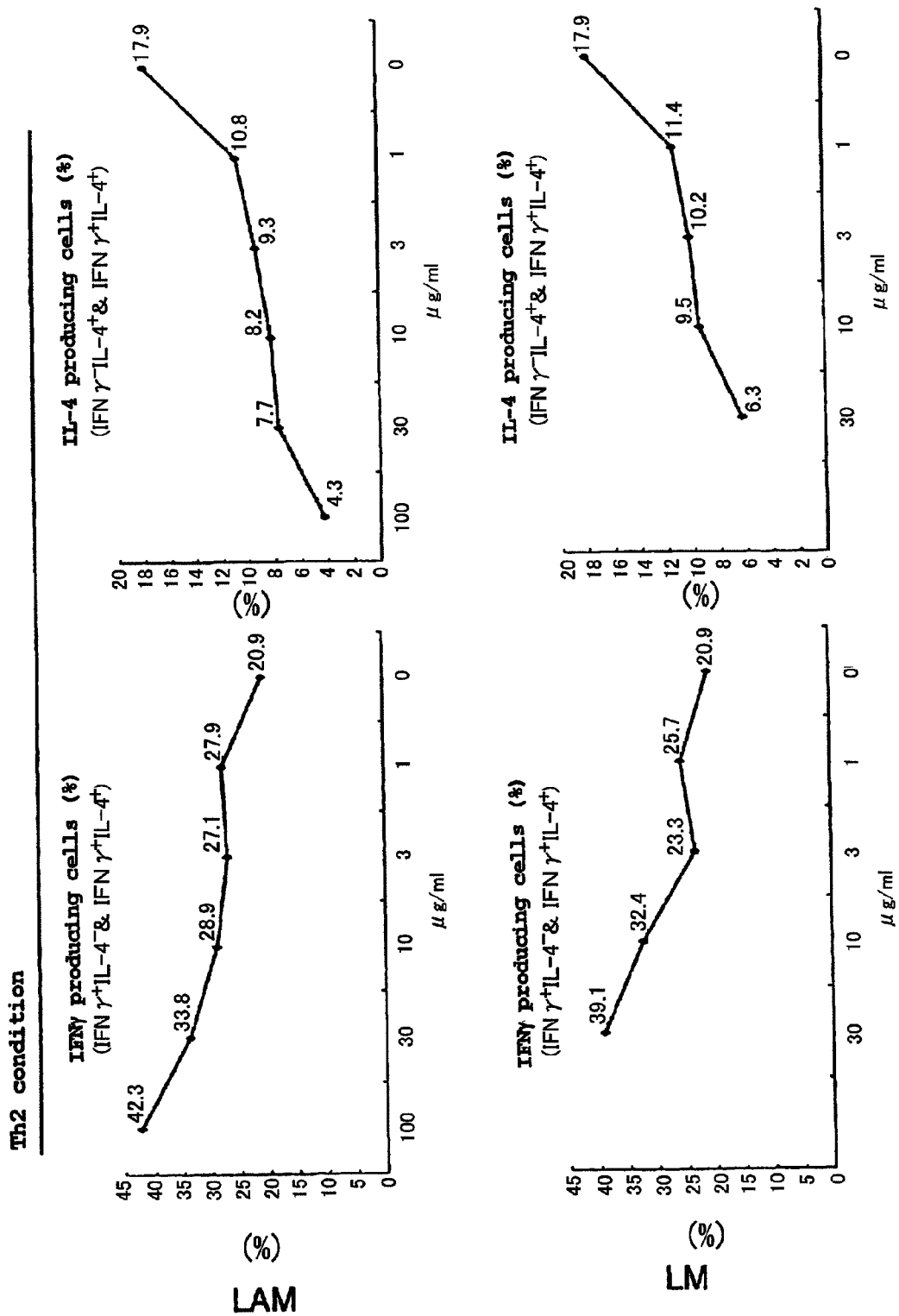
FIG. 13 shows the effects of LAM and LM on the number of IFNγ-producing cells and the number of IL-4-producing cells under Th2 differentiation inducing conditions.

The results of tests under Th2 differentiation inducing conditions are shown in FIGS. 12 and 13 and Table 6.

TABLE 6

| | ビヒクル | CW (30 μg/ml) | LAM/LM (30 μg/ml) | LM (3 μg/ml) | LM (30 μg/ml) | LAM (3 μg/ml) | LAM (30 μg/ml) |
|---|---|---|---|---|---|---|---|
| IFNγ⁺IL-4⁻ cells (%) | 18.1 | 32.3 | 52.6 | 29.5 | 38.4 | 26.9 | 34.8 |
| IFNγ⁻IL-4⁺ cells (%) | 19.4 | 15.9 | 6.2 | 14.3 | 8.8 | 17.2 | 11.9 |

Under Th2 differentiation inducing conditions, each of LAM and LM dose-dependently increased the ratio of IFNγ-producing cells, and dose-dependently suppressed the ratio of IL-4-producing cells (FIG. 13). These effects were more potent when the LAM/LM mixture was used than when LAM or LM was used alone (Table 6). Hence, it was demonstrated that even in Th2 differentiation induction, LAM and LM enhance the induction of IFNγ-producing cells, and suppress the induction of IL-4-producing cells when used alone, and that by mixing LAM and LM, these effects are synergistically enhanced.

INDUSTRIAL APPLICABILITY

Because the LAMs and LMs contained in BCG cell bodies enhance Th1 immune responses and suppress Th2 immune responses, they are useful as prophylactic/therapeutic agents for cancers and the like, also as adjuvants for anti-infectious disease vaccines such as antituberculotic vaccines, and still also as therapeutic agents for allergic diseases such as pollinosis.

The invention claimed is:

1. A method of promoting the differentiation of human CD4T cells into Th1 cells, comprising culturing human CD4T cells in a medium containing a stimulating-amount of antigen, IL-12, and lipoarabinomannans and/or lipomannans derived from BCG cell bodies, thereby promoting differentiation of the human CD4T cells into Th1 cells.

2. A method of suppressing the differentiation of human CD4T cells into Th2 cells, comprising culturing human CD4T cells in a medium containing a stimulating-amount of antigen, IL-4, and lipoarabinomannans and/or lipomannans derived from BCG cell bodies, thereby suppressing the differentiation of the human CD4T cells into Th2 cells.

3. The method of claim 2, wherein the medium further comprises antigen-presenting cells.

4. A method for treating allergic disease in a mammal, comprising administering an effective amount of
 (i) lipomannans derived from BCG cell bodies or
 (ii) lipoarabinomannans derived from BCG cell bodies and lipomannans derived from BCG cell bodies
 to the mammal, thereby treating allergic disease in the mammal.

5. The method of claim 1, wherein the medium does not comprise antigen-presenting cells.

6. The method of claim 1, wherein the medium comprises a combination of lipoarabinomannans derived from BCG cell bodies and lipomannans derived from BCG cell bodies.

7. The method of claim 1, wherein at least one of the lipomannans is a triacyllipomannan, wherein the number of mannose residues in the triacyllipomannan is 20 to 48.

8. The method of claim 7, wherein the triacyllipomannan is a compound represented by the formula:
wherein each of $R_1$, $R_2$, and $R_3$, whether identical or different, is an acyl group having 14 to 20 carbon atoms, m represents an integer of 1 to 22, and n represents an integer of 1 to 10.

9. The method of claim 2, wherein the medium comprises a combination of lipoarabinomannans derived from BCG cell bodies and lipomannans derived from BCG cell bodies.

10. The method of claim 2, wherein at least one of the lipomannans is a triacyllipomannan, wherein the number of mannose residues in the triacyllipomannan is 20 to 48.

11. The method of claim 10, wherein the triacyllipomannan is a compound represented by the formula:

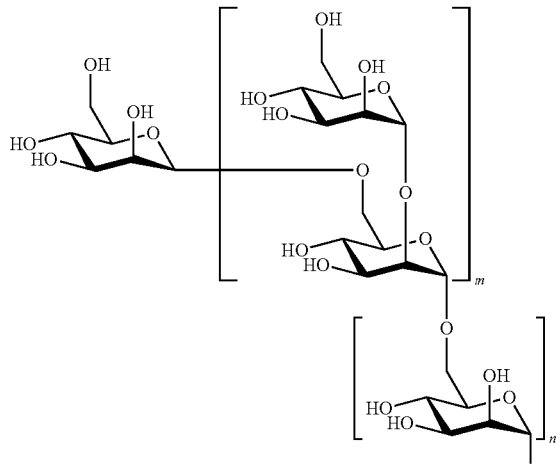

-continued

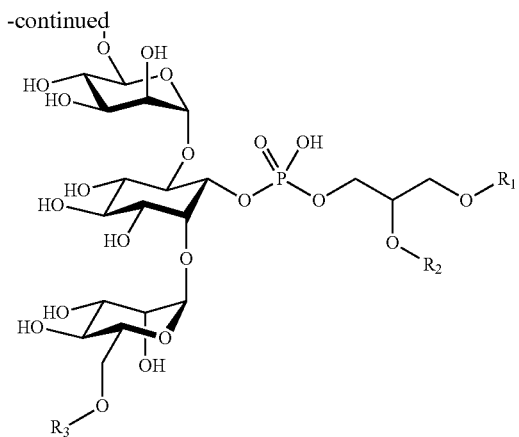

wherein each of $R_1$, $R_2$, and $R_3$, whether identical or different, is an acyl group having 14 to 20 carbon atoms, m represents an integer of 1 to 22, and n represents an integer of 1 to 10.

12. The method of claim 4, wherein an effective amount of the lipoarabinomannans derived from BCG cell bodies and the lipomannans derived from BCG cell bodies is administered to the mammal.

13. The method of claim 4, wherein at least one of the lipomannans is a triacyllipomannan, wherein the number of mannose residues in the triacyllipomannan is 20 to 48.

14. The method of claim 13, wherein the triacyllipomannan is a compound represented by the formula:

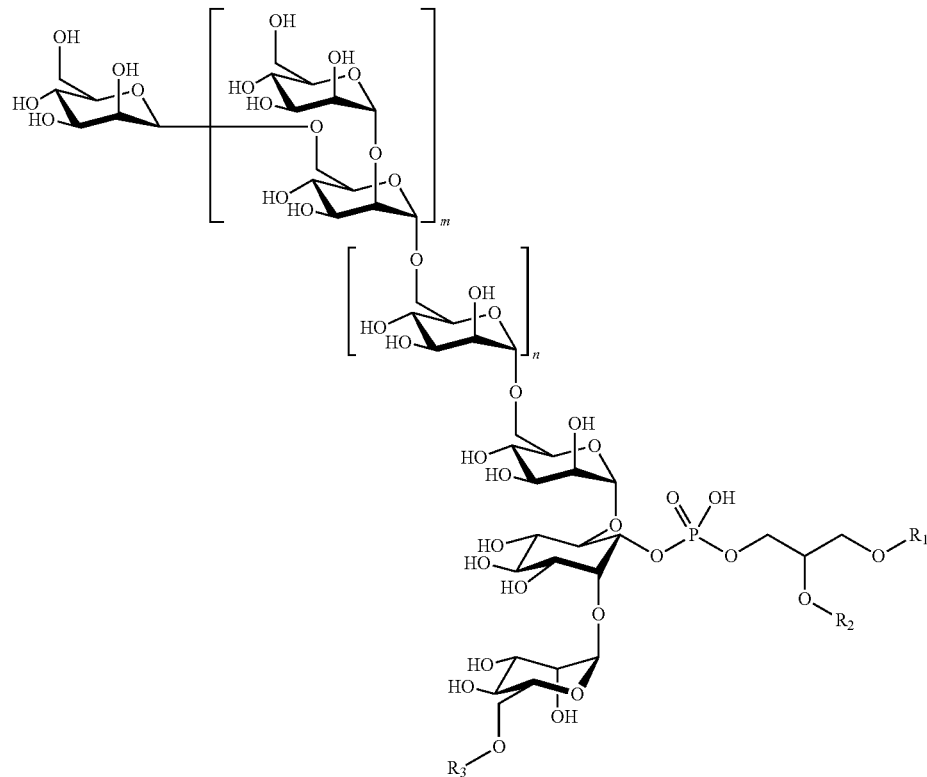

wherein each of $R_1$, $R_2$, and $R_3$, whether identical or different, is an acyl group having 14 to 20 carbon atoms, m represents an integer of 1 to 22, and n represents an integer of 1 to 10.

* * * * *

UNITED STATES PATENT AND TRADEMARK OFFICE
CERTIFICATE OF CORRECTION

| | | |
|---|---|---|
| PATENT NO. | : 7,928,088 B2 | Page 1 of 1 |
| APPLICATION NO. | : 11/939920 | |
| DATED | : April 19, 2011 | |
| INVENTOR(S) | : Taniguchi et al. | |

It is certified that error appears in the above-identified patent and that said Letters Patent is hereby corrected as shown below:

IN THE CLAIMS

Insert the following formula in claim 8, at column 28, between lines 35 and 36, immediately after the phrase "a compound represented by the formula:":

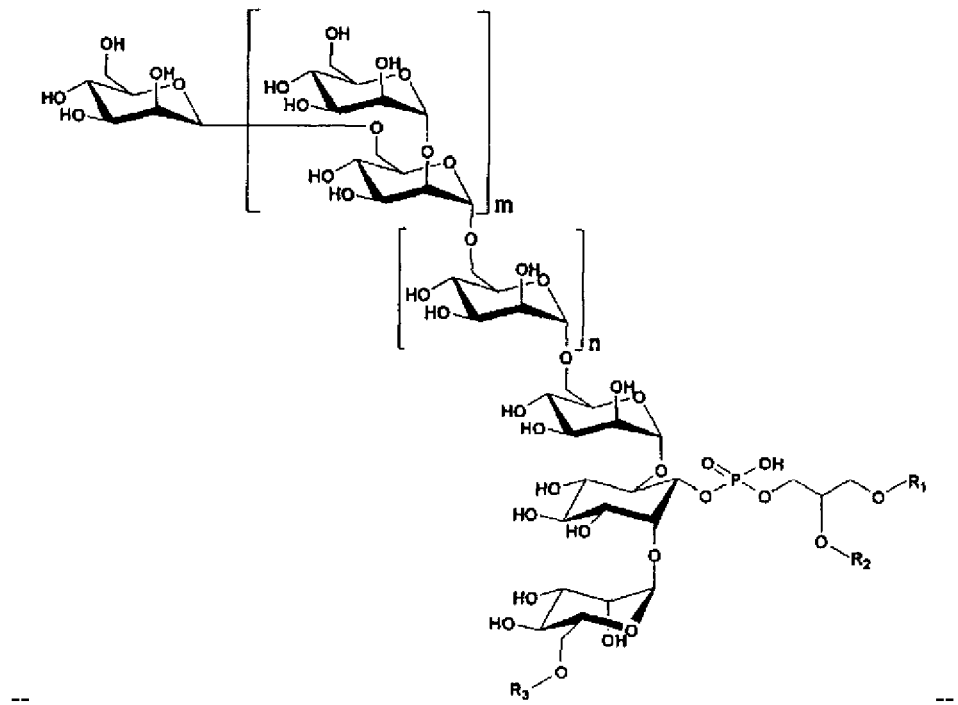

--                                                                                --

Signed and Sealed this
Eleventh Day of October, 2011

David J. Kappos
*Director of the United States Patent and Trademark Office*